US012629265B2

(12) United States Patent
Jensen et al.

(10) Patent No.: US 12,629,265 B2
(45) Date of Patent: May 19, 2026

(54) BONE GRAFT DELIVERY SYSTEM, COMPONENTS AND METHOD OF USE OF SAME

(71) Applicant: Arthrex, Inc., Naples, FL (US)

(72) Inventors: Wade Jensen, Dakota Dunes, SD (US);
Joshua Karnes, Estero, FL (US);
Michael Esaia, Naples, FL (US);
Shane Noble, Naples, FL (US)

(73) Assignee: Arthrex, Inc., Naples, FL (US)

( * ) Notice: Subject to any disclaimer, the term of this patent is extended or adjusted under 35 U.S.C. 154(b) by 239 days.

(21) Appl. No.: 18/586,303

(22) Filed: Feb. 23, 2024

(65) Prior Publication Data

US 2024/0285415 A1 Aug. 29, 2024

Related U.S. Application Data

(60) Provisional application No. 63/486,715, filed on Feb. 24, 2023.

(51) Int. Cl.
*A61F 2/46* (2006.01)
*A61F 2/28* (2006.01)

(52) U.S. Cl.
CPC .......... *A61F 2/4601* (2013.01); *A61F 2/4611* (2013.01); *A61F 2002/2835* (2013.01)

(58) Field of Classification Search
CPC ........... A61B 17/8805; A61B 17/8811; A61B 17/8816; A61B 17/8819; A61B 17/8822; A61F 2/4601; A61F 2/4611
See application file for complete search history.

(56) References Cited

U.S. PATENT DOCUMENTS

| | | | |
|---|---|---|---|
| 6,436,068 B1 * | 8/2002 | Bardy ............... | A61M 37/0069 604/59 |
| 6,439,439 B1 | 8/2002 | Rickard et al. | |
| 7,014,640 B2 | 3/2006 | Kemppainen et al. | |
| 7,909,833 B2 * | 3/2011 | Voellmicke ........ | A61B 17/8822 606/94 |
| 8,062,304 B2 | 11/2011 | Blain et al. | |
| 8,096,975 B2 * | 1/2012 | Lewis ................ | A61B 17/8836 604/113 |
| 8,251,946 B2 * | 8/2012 | Bardy ............... | A61M 37/0069 604/60 |
| 8,394,050 B2 * | 3/2013 | Bardy ............... | A61M 37/0069 604/60 |
| 8,696,678 B2 | 4/2014 | Foster | |
| 8,900,312 B2 | 12/2014 | Mclean et al. | |
| 9,545,282 B2 * | 1/2017 | Mathur ................ | A61F 2/4611 |
| 9,833,248 B2 * | 12/2017 | Budyansky ........ | A61B 17/3472 |
| 10,687,828 B2 * | 6/2020 | Greenhalgh ....... | A61B 17/1671 |
| 10,687,879 B2 * | 6/2020 | Dewey .............. | A61B 17/8822 |
| 10,709,576 B2 * | 7/2020 | Shimko .............. | A61B 17/8863 |
| 10,945,860 B2 * | 3/2021 | Hay ...................... | A61F 2/4601 |
| 10,973,656 B2 | 4/2021 | Kleiner et al. | |

(Continued)

OTHER PUBLICATIONS

International Search Report and Written Opinion for PCT/US2024/ 017168, mailed Aug. 5, 2024, 21 pages.

*Primary Examiner* — Anu Ramana
(74) *Attorney, Agent, or Firm* — Cozen O'Connor

(57) ABSTRACT

Provided herein are bone graft delivery systems comprising a flexible plunger, a delivery gun, and a detachable offset cannula. Methods of delivering bone graft material using the bone graft delivery systems are also provided.

17 Claims, 28 Drawing Sheets

(56) References Cited

U.S. PATENT DOCUMENTS

| | | | | |
|---|---|---|---|---|
| 11,253,374 B2 * | 2/2022 | Krause | ............... | A61B 17/3421 |
| 11,529,179 B2 * | 12/2022 | Deridder | ............ | A61B 17/8822 |
| 12,329,430 B2 * | 6/2025 | Reves | ................ | A61B 17/8819 |
| 2008/0300540 A1 * | 12/2008 | Lewis | ................ | A61B 17/8836 |
| | | | | 604/113 |
| 2014/0324013 A1 * | 10/2014 | Shadeck | ............ | A61B 17/8816 |
| | | | | 604/154 |
| 2015/0112352 A1 * | 4/2015 | Krause | ................. | A61F 2/4601 |
| | | | | 606/279 |
| 2016/0296344 A1 | 10/2016 | Greenhalgh et al. | | |
| 2018/0125558 A1 | 5/2018 | Flores et al. | | |
| 2020/0275965 A1 * | 9/2020 | Deridder | ............ | A61B 17/8819 |
| 2020/0330242 A1 | 10/2020 | Hay | | |
| 2023/0059830 A1 * | 2/2023 | Milella | ................. | A61F 2/4465 |
| 2024/0215992 A1 * | 7/2024 | Budyansky | ........... | A61F 2/4601 |

* cited by examiner

1

BONE GRAFT DELIVERY SYSTEM, COMPONENTS AND METHOD OF USE OF SAME

PRIORITY CLAIM

The present application claims priority to U.S. Provisional Patent Application No. 63/486,715, filed Feb. 24, 2023, the disclosure of which is hereby incorporated herein, in its entirety, by reference.

BACKGROUND

Minimally invasive procedures, such as minimally invasive spinal fusion procedures, often involve the use of a working cannula. The working cannula may be as wide as 1.5 inches, to gain access to the anatomy to be treated during the procedure. Multiple instruments may be used simultaneously during the procedure, and instrument geometry may cause collisions and impair visualization making the procedure unnecessarily challenging. Devices are needed in the art to provide better visualization and reduce complexity for minimally invasive procedures.

BRIEF SUMMARY

Some embodiments described herein provide a bone graft delivery system with a cannula that defines a non-linear delivery path from a delivery gun to a delivery location. The non-linear delivery path facilitates positioning of the delivery gun such that reduced visibility of the delivery location due to the delivery gun blocking line-of-sight is improved compared to other bone graft delivery devices that have a linear delivery path. Additional embodiments described herein include components and methods of loading bone graft into a cannula, and methods of assembly, use, and cleaning of the bone graft delivery system.

Some embodiments described herein include a bone graft delivery system including a delivery gun with a proximal end, a distal end, and a body extending therebetween. The body defines a first lumen extending through the body from the proximal end to the distal end along a longitudinal axis. The bone graft delivery system further includes a cannula coupled to the distal end of the delivery gun, and the cannula defines a second lumen extending through the cannula along a first portion that is aligned with the longitudinal axis, and a second portion that is angularly offset from the longitudinal axis. Additionally, the bone graft delivery system includes a flexible plunger sized to be insertable into the first lumen through an opening defined by the proximal end. The flexible plunger is movable to a position wherein a distal portion of the flexible plunger is within the second portion of the second lumen and a proximal portion of the flexible plunger is within the first lumen.

An embodiment described herein includes a bone graft delivery system comprising (a) a flexible plunger; (b) a delivery gun comprising a proximal end, a distal end, a body having a lumen, a stationary handle, a trigger, and a longitudinal axis. The body of the delivery gun comprises a first circumferential engagement mechanism and a second circumferential engagement mechanism each having teeth or threads that encircle the lumen and that can contact the flexible plunger around its circumference when present in the lumen of the delivery gun. When the trigger is engaged the first circumferential engagement mechanism is forced forward and down onto the flexible plunger to advance the flexible plunger, and wherein the second circumferential engagement mechanism can accept the flexible plunger as it moves forward and prevents backward movement of the flexible plunger.

The bone graft delivery system can further comprise (c) a detachable offset cannula that can be connected to the distal end of the delivery gun. The offset cannula comprises a first portion that is in line with the longitudinal axis of the delivery gun, and a second portion that is offset from the longitudinal axis of the delivery gun. The detachable offset cannula has an oval shaped opening tip at its distal end, and the detachable offset cannula can be removed from the delivery gun without removing the plunger from the delivery gun.

The first circumferential engagement mechanism and the second circumferential engagement mechanism can each have a conical shape or a cylindrical shape. The delivery system can further comprise a U shaped sled for delivery of bone graft material to the offset cannula. The offset cannula, a front assembly, and a back assembly of the delivery gun can be detached so that the delivery gun can be cleaned and reused.

According to some embodiments, a method of delivering bone graft material includes loading bone graft material into a lumen of a cannula; moving a distal tip of a flexible plunger through an opening formed in a proximal end of the delivery gun; moving the distal tip of the flexible plunger through a lumen of the delivery gun, toward a distal end of the delivery gun, along a longitudinal axis; moving the distal tip of the flexible plunger through the distal end and into the lumen of the cannula; moving the distal tip through a first portion of the cannula along the longitudinal axis; moving the distal tip through a second portion of the cannula along a direction that is angularly offset from the longitudinal axis; and pushing the loaded graft material out of the lumen of the cannula with the distal tip of the flexible plunger.

Some embodiments provided herein include methods of using bone graft delivery systems. The methods can comprise loading the detachable offset cannula with bone graft material using a delivery sled, attaching the detachable offset cannula to a connector on a distal end of the delivery gun, and inserting the flexible plunger into the lumen of the delivery gun. The method can further comprise guiding the oval shaped opening tip of the detachable offset cannula of the bone graft delivery system to the desired site, and depressing the trigger such that the bone graft material is delivered through the oval shaped opening tip of the detachable offset cannula to the desired site. Methods can further comprise activating the disengagement mechanism to release the flexible plunger, and using the connector to remove the offset cannula from the delivery gun.

Some embodiments provided herein comprise methods of delivering bone graft material to a surgical site. The methods can include guiding the oval shaped opening tip of the detachable offset cannula of the bone graft delivery systems as described herein to the surgical site, activating the trigger, and delivering bone graft material to the surgical site.

Some embodiments herein provide a bone graft loader including a sled and a push rod. The sled includes an elongate body having a tubular member defining a channel extending therethrough. The elongate body further includes a collar extending from the tubular member, and the collar defines a collar track extending into the collar toward the tubular member. The collar track includes a non-linear portion. The push rod includes an elongate body with a rod portion shaped to correspond to the channel such that the rod portion is slidable within the channel. The elongate body of the push rod further includes a handle extending from the rod portion, and a projection shaped to follow the non-linear portion of the collar track.

An embodiment of the disclosure is directed to a kit including a delivery gun, a cannula, and a flexible plunger. The delivery gun includes a proximal end, a distal end, and a body extending therebetween, and the body defines a first lumen extending through the body from the proximal end to the distal end along a longitudinal axis. The cannula is couplable to the distal end of the delivery gun, and the defines a second lumen extending through the cannula along a path that includes a non-linear portion. The flexible plunger is sized to be insertable into the first lumen through an opening defined by the proximal end, is further sized to be insertable into the second lumen, and is flexible enough to follow the non-linear portion of the path.

A kit, according to some embodiments, can include (a) a flexible plunger, and (b) a delivery gun comprising a proximal end, a distal end, a body having a lumen, a stationary handle, a trigger, and a longitudinal axis. The body of the delivery gun comprises a first circumferential engagement mechanism and a second circumferential engagement mechanism each having teeth or threads that encircle the lumen and that can contact the flexible plunger around its circumference when present in the cannula of the delivery gun.

When the trigger is engaged, the first circumferential engagement mechanism is forced forward and down onto the flexible plunger to advance the flexible plunger, and the second circumferential engagement mechanism can accept the flexible plunger as it moves forward and prevent backward movement of the flexible plunger. The kit can further include (c) a detachable offset cannula that can be connected to the distal end of the delivery gun. The offset cannula comprises a first portion that is in line with the longitudinal axis of the delivery gun, and a second portion that is offset from the longitudinal axis of the delivery gun. The detachable offset cannula has an oval shaped opening tip at its distal end. The kit can further include one or more of: (d) one or more delivery sleds, (e) one or more delivery tools, or (f) one or more types of bone graft materials.

Some embodiments of the disclosure include bone graft delivery systems comprising (a) a flexible plunger and (b) a delivery gun comprising a proximal end, a distal end, a body having a lumen, a stationary handle, a trigger, and a longitudinal axis. The body of the delivery gun comprises a first circumferential engagement mechanism having teeth or threads that encircle the lumen and that can contact the flexible plunger around its circumference when present in the lumen of the delivery gun. When the trigger is engaged the first circumferential engagement mechanism is forced forward and down onto the flexible plunger to advance the flexible plunger.

The bone graft delivery systems can further include (c) a detachable offset cannula that can be connected to the distal end of the delivery gun. The offset cannula comprises a first portion that is in line with the longitudinal axis of the delivery gun, and a second portion that is offset from the longitudinal axis of the delivery gun. The detachable offset cannula has an opening tip at its distal end. The detachable offset cannula can be removed from the delivery gun without removing the plunger from the delivery gun.

The first circumferential engagement mechanism can have a conical shape or a cylindrical shape. The delivery systems can further comprise a U shaped sled for delivery of bone graft material to the offset cannula. The offset cannula, a front assembly, and a back assembly can be detached from the delivery gun so that the delivery gun can be cleaned and reused.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings. The headings and Abstract of the Disclosure provided herein are for convenience only and do not interpret the scope or meaning of the embodiments.

DETAILED DESCRIPTION

Figure 1:
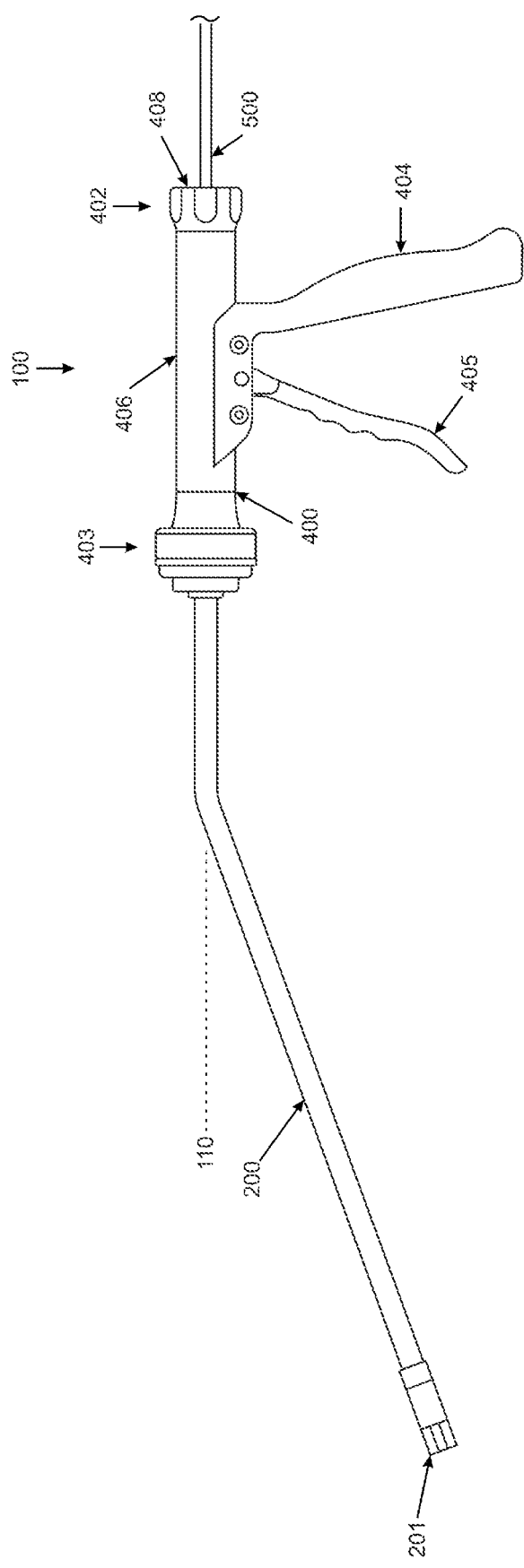
FIG. 1 shows a bone graft delivery device having a plunger, a delivery gun, and an offset cannula.
Figure 2:
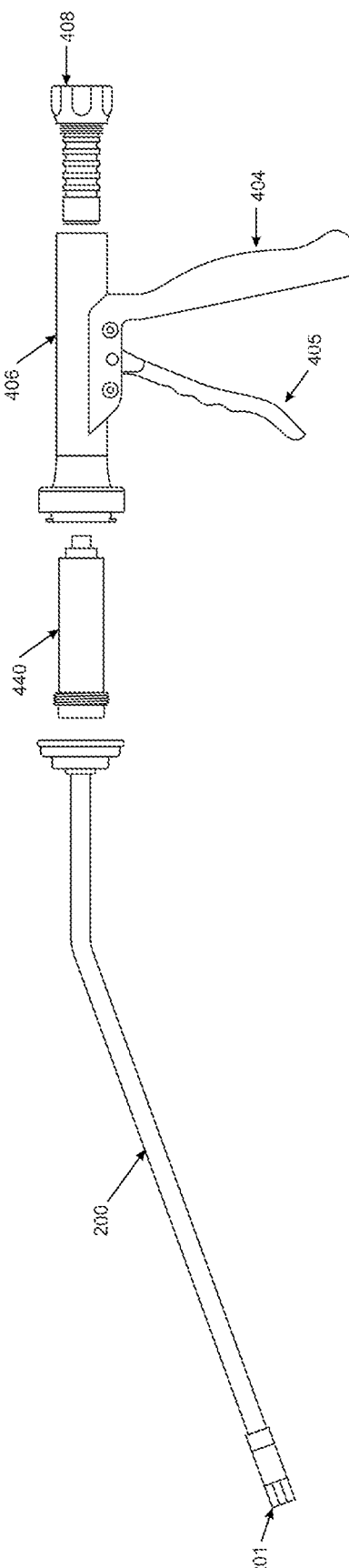
FIG. 2 shows a disassembled bone graft delivery device.
Figure 3:
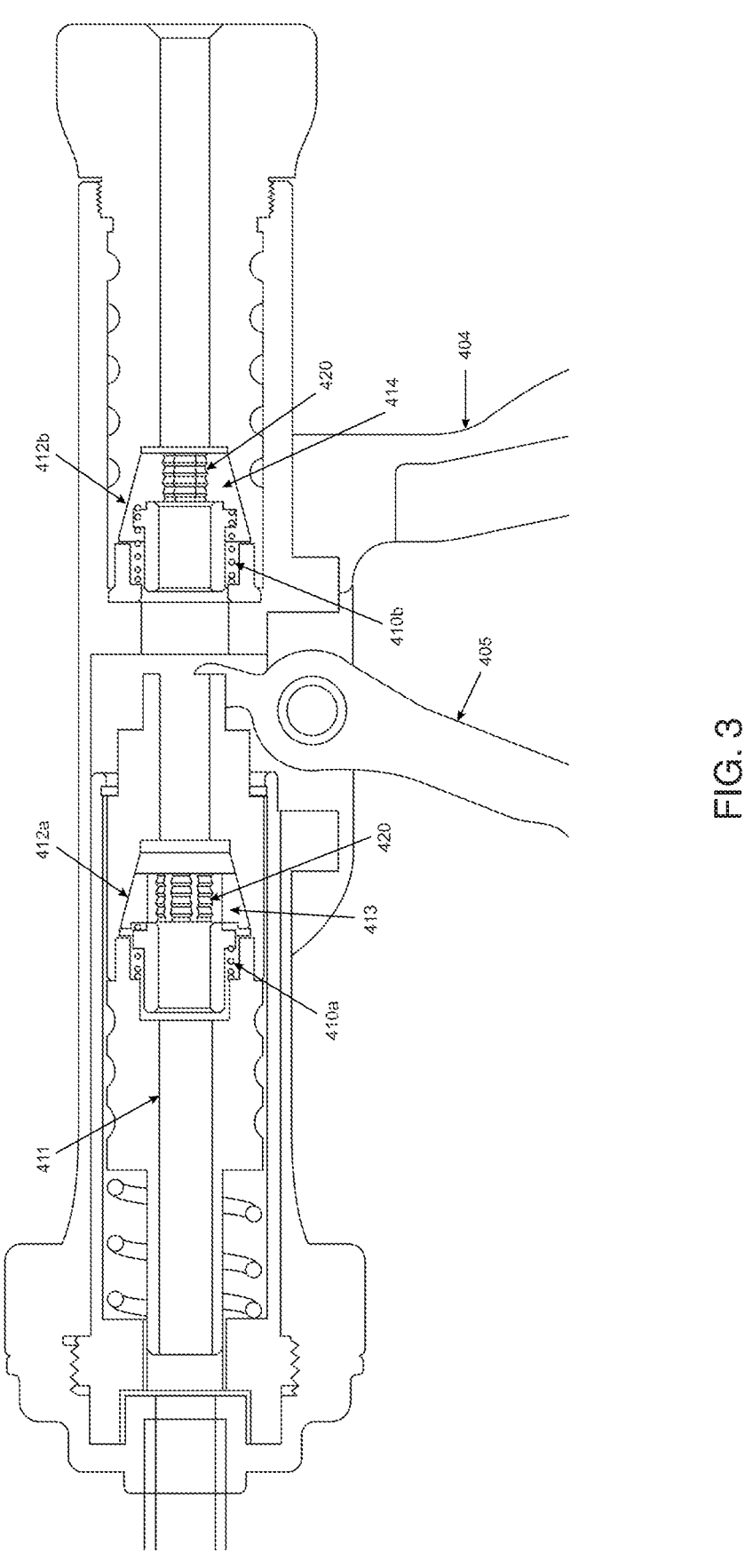
FIG. 3 shows the interior of a delivery gun without a plunger.

Provided herein are devices and methods of use for delivery of bone graft material in minimally invasive spine procedures. A device can comprise, inter alia, a delivery gun, a plunger, and an offset cannula.

Bone graft material is often delivered to a surgical site (e.g., an intervertebral disc space) through a small opening. The linear delivery path of known devices may result in a reduction of visibility at the surgical site. The bone graft delivery system described herein may include a bent or offset cannula that provides a non-linear pathway for the bone graft material to follow as it is delivered to the surgical site. The non-linear pathway enables the user of the bone graft delivery system to position the components offset from the line of sight to the surgical site, thereby improving visibility during a surgical procedure.

The bone graft delivery system may also include a flexible plunger that advances the bone graft material along the non-linear pathway. To improve cleaning and reusability of the bone graft delivery system, some embodiments described herein include an advancement/engagement assembly that only permits one-way movement (e.g., distally) of the flexible plunger. This prevents the distal portion of the flexible plunger, which contacts the bone graft material, from traveling back through the interior components of the bone graft delivery system and while carrying bits of the bone graft material.

Additionally, the bone graft delivery system according to some embodiment, is able to be disassembled to further enhance the cleaning/sterilization process. For example, the cannula may be removable from a delivery gun, through which the flexible plunger advances, without first needing to remove the plunger from either the cannula or the delivery gun. Additionally, the internal components of the delivery gun, such as the advancement/engagement assembly, may be removable from the body of the delivery gun. When disassembled, the components may be placed in a sterilization case that reliably cleans/sterilizes the components.

Some embodiments of the bone graft delivery system may include a deflector that is positioned so as to deflect uninserted portions of the flexible plunger away from the user of the bone graft delivery system, thereby preventing contact with a non-sterile portion of the operating field.

Referring to FIGS. 1 to 4, a delivery gun 400 can have a proximal end 402 and a distal end 403, a stationary handle 404 and a trigger 405 that can engage a first circumferential engagement mechanism 413 located within a barrel or lumen 411 (referred to hereinafter as the lumen) of a body 406 of the delivery gun 400. In an optional aspect, the proximal end 402 of the delivery gun 400 can comprise a disengagement mechanism, which can be used to connect or disengage the plunger 500 from the delivery gun 400.

The distal end 403 of the delivery gun 400 can comprise a connector, which can be used to connect or disengage the offset cannula 200 from the delivery gun 400. The connector can be made of any material (e.g., plastic or metal) and be, e.g., screw threads, press fit mechanism or any other suitable connector.

The body of the delivery gun 400 can have the lumen 411 running down its longitudinal axis 110. The first circumferential engagement mechanism 413 and a second circumferential engagement mechanism 414 may each include teeth or threads (e.g., spiral thread, V-thread, square thread, acme head thread, etc.) that encircle (e.g., partially or completely) the lumen 411 and the longitudinal axis 110 therewithin, and that contact the plunger 500 around its circumference (e.g., a portion or an entirety) when the plunger 500 is present within the lumen 411 of the delivery gun 400.

When the trigger 405 is engaged or depressed, the first circumferential engagement mechanism 413 can be forced forward and down (e.g., clamping) onto the plunger 500 within the lumen 411 of the body to advance the plunger 500 forward (distally) toward the offset cannula 200. The second circumferential engagement mechanism 414 can allow passage of the plunger 500 therethrough as the plunger 500 moves forward (distally) and prevent backward movement of the plunger 500 (proximally).

The first and/or second circumferential engagement mechanism(s) 413, 414 can provide for a more robust engagement with the plunger 500 and decreased stress on the plunger 500 as compared to a one-sided engagement, which pushes a plunger solely from a distal end of a plunger. A circumferential engagement can be self-reinforcing such that the more force applied to the distal tip or end of the plunger 500, the higher the normal force at the engagement location.

According to one or more embodiments, the delivery gun 400 comprises a lumen 411 through which a plunger (e.g., the plunger 500) can fit. The delivery gun 400 can further comprise the first circumferential engagement mechanism 413, which is actuated by the trigger 405 operated by the user. The first circumferential engagement mechanism 413 can have a ramp 412a, which may be a three-dimensional cone shape encircling the lumen 411, and teeth or threads 420 that engage with the plunger 500. The cone shape allows for the engagement of the outer circumference (e.g., a majority of the outer circumference) of the plunger 500.

In an alternative embodiment, the first circumferential engagement mechanism 413 does not have a ramp and instead is a cylindrical shape encircling the lumen 411 with teeth or threads 420 that engage with the plunger 500. The teeth or threads 420 can engage with the teeth or threads of the plunger 500. When the trigger 405 is squeezed by a user, the first circumferential engagement mechanism 414 may be forced forward and down onto the plunger 500 (e.g., exerting a compressive force). The teeth or threads 420 of the first and second circumferential engagement mechanisms 413, 414 encircle (e.g., partially or completely) the plunger 500 and can contact the plunger 500 around its circumference (e.g., up to an entirety of its circumference). The teeth or threads 420 of the first circumferential engagement mechanism 413 may engage with teeth or threads on the plunger 500 to move the plunger 500 forward (e.g., distally).

A second circumferential engagement mechanism 414 can have a ramp 412b, which may be a three-dimensional cone shape encircling the lumen 411, and teeth or threads that can engage with the plunger 500. In an alternative embodiment, the second circumferential engagement mechanism 414 does not have a ramp and instead is a cylindrical shape encircling the lumen 411 with teeth or threads 420 that engage with the plunger 500.

When the plunger is pushed forward by the first circumferential engagement mechanism 413, the teeth or threads of the second circumferential engagement mechanism 414 engage with the plunger such that the plunger cannot move backward towards the proximal end 402 of the delivery gun 400. The second circumferential engagement mechanism 414 therefore acts as a self-reinforcing mechanism. The second circumferential engagement mechanism 414 can be absent in some aspects. The first circumferential engagement mechanism 413 may include a spring 410a and the second circumferential engagement mechanism 414 may include a spring 410b to exert a biasing force against the teeth or threads that engage with the plunger 500. According to one embodiment, the springs 410a and 410b may be teeth springs.

According to one embodiment, the plunger 500 can have teeth that interact with threads or teeth of an engagement mechanism (e.g., the first circumferential engagement mechanism 413 or the second circumferential engagement mechanism 414) such that the plunger 500 is moved through an engagement mechanism and into the offset cannula 200 via rotation of the plunger 500 instead of through the use of the trigger 405. The plunger 500 may only be movable forward through the body of the delivery gun, according to some embodiments. After use, the plunger 500 can be pulled through the distal end 403 of the delivery gun 400.

The circumferential engagement mechanisms can be disconnected to allow for manual moment of the plunger 500 within the lumen 411 or the body 406 of the delivery gun 400, according to one embodiment. The detachable offset cannula 200 can be removed from the delivery gun 400 without removing the plunger 500 from the delivery gun 400. In some aspects the body 406 of the delivery gun 400 can be disassembled for cleaning. For example, the offset cannula 200 can be disconnected from the body 406 of the delivery gun 400, and the back assembly 408 and the front assembly 440 can be removed before re-sterilization for further use. In this way the entire device can be easily cleaned.

Referring to FIGS. 1 to 3 and 6, an offset cannula 200 comprises a distal end 208 and a proximal end 204. The distal end comprises a delivery tip 201 and the proximal end can connect to the delivery gun 400 at the distal end 403 of the delivery gun 400. The delivery cannula can be detachable from the delivery gun via a connector. An offset delivery cannula can have a first portion 205 that is on the same longitudinal axis 110 of the delivery gun and a second portion 206 that is offset from the longitudinal axis at an angle 203. The angle can be any suitable angle, for example, 95, 100, 110, 120, 130, 140, 150, 160, 170 degrees or more.

The offset cannula can be flexible or hinged such that the angle can be changed by the user. A hinge can be present between the first and second portions of the delivery cannula. The offset angle of the cannula can comprise a gradual bend (e.g., a semi-circular or partially circular bend) or an acute bend. The offset cannula can have an inlet 209, which can be loaded with graft material using a delivery sled 600 (shown in FIG. 5).

The cross-section of the cannula can be circular, oval, or any other suitable shape. According to one embodiment, the cross-section of the cannula is circular over the length of the cannula, except for the tip, which can have an oval cross-section. According to another embodiment, the cross-section of the cannula is circular over the length of the cannula, including the tip, which can also have a circular cross-section. Alternatively, the cannula may be circular or oval over the length of the cannula and the tip has an oval opening. There may be no change in the internal cross section of the cannula as it transitions into the tip. This prevents "necking" or increased back pressure, which can lead to jamming.

An oval opening of the tip can have an outer diameter of about 4, 5, 6, or 7 mm in the cranial/caudal direction and an outer diameter of about 8, 9, 10, 11, or 12 mm in the medial/lateral direction. An oval opening of the tip can have an outer diameter of about 6 mm in the cranial/caudal direction and an outer diameter of about 8 to about 10 mm in the medial/lateral direction. A circular opening of the tip can have an outer diameter of about 4-12 mm (e.g., about 4, 5, 6, 7, 8, 9, 10, 11, 12 mm or more).

The offset cannula can advantageously allow a user direct visualization of graft delivery when decompression tubes are used.

Figure 5:
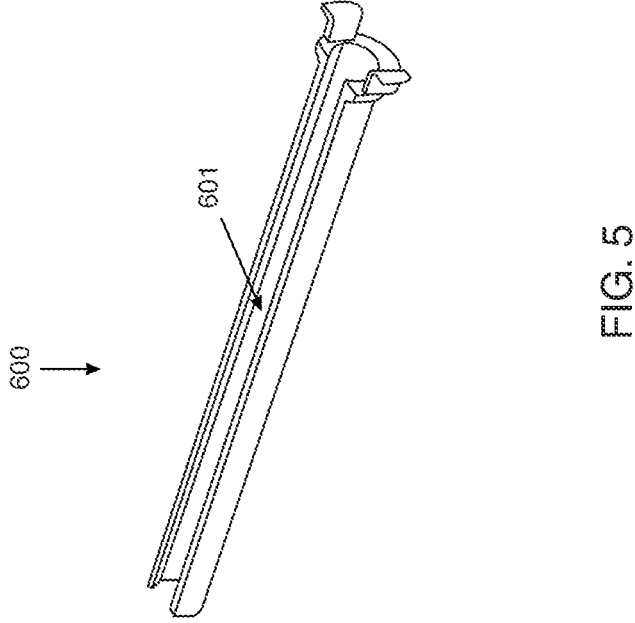
FIG. 5 shows a delivery sled.

Referring to FIG. 5, a delivery sled 600 can be connected to or brought into proximity of an offset cannula to load the offset cannula with graft material. As shown, the delivery sled may have a parabola, arc, or "U" shaped cross section. A top 601 of the delivery sled may be open to facilitate quick delivery of the graft material into the offset cannula. A tool such as a spatula, plunger, or rod that can be about the same length of the delivery sled can be used to push the graft material from the delivery sled and into the offset cannula. The delivery sled 600 can be connected to the offset cannula for delivery of the graft material by, for example screw threads, a press fit mechanism, or a slot and key mechanism.

Figure 4:
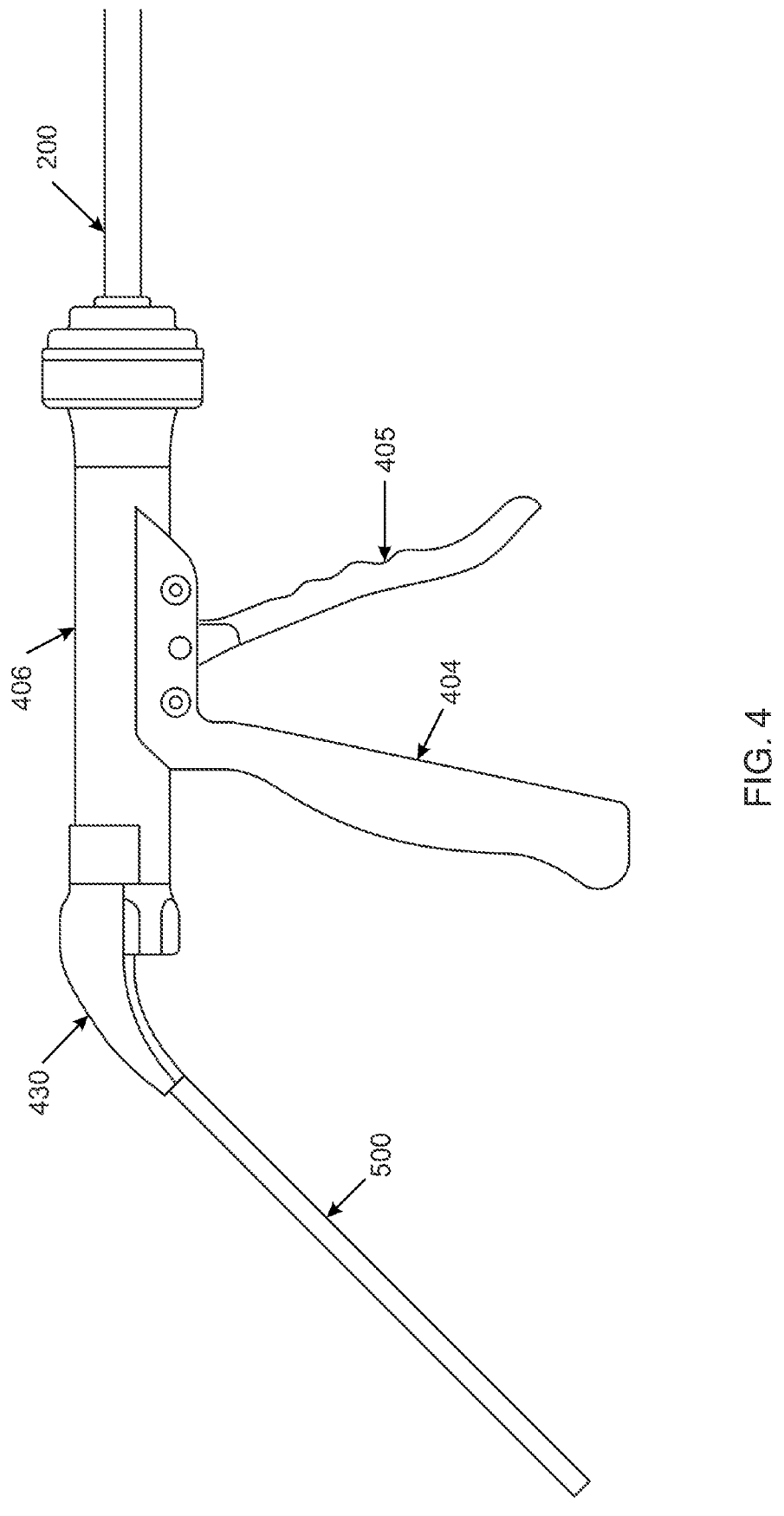
FIG. 4 shows a bone graft delivery device with a deflection shield for the plunger.
Figure 6:
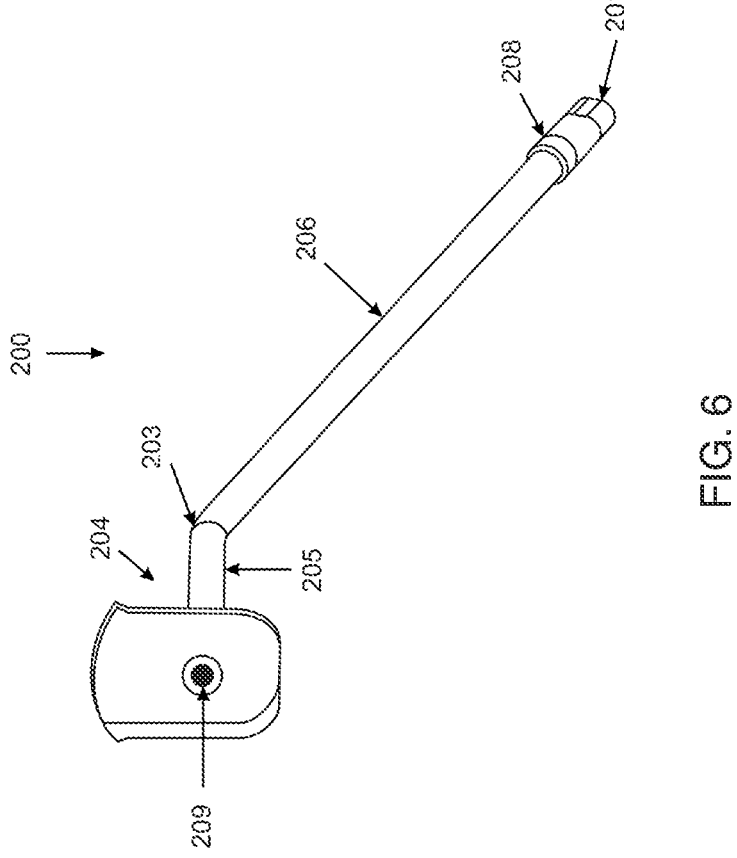
FIG. 6 shows an offset cannula.

Referring to FIGS. 1 and 4, a plunger 500 can be inserted into the proximal end 402 of the delivery gun 400. The plunger 500 can be flexible such that it can move through the angle or bend of the offset cannula. The flexible plunger 500 can be advanced by the delivery gun and through the delivery gun into the proximal end 204 of the offset cannula 200 and through the cannula all the way to the delivery tip 201 of the cannula. The flexible plunger can move through the angle 203 of the cannula due to the flexibility of the plunger. Where both the cannula and plunger are flexible, the flexible cannula can have more rigidity than the flexible plunger. The flexible cannula and/or plunger can be made of plastic, nylon, or any other suitable method.

A plunger can have teeth or threads (e.g., spiral thread, V-thread, square thread, acme head thread, etc.) to engage with the teeth or threads of the delivery gun. A plunger can have threads to engage with threads or teeth or threads of a circumferential engagement mechanism of a delivery gun.

The plunger may be docked in a non-linear or off-axis position from the longitudinal axis 110 of the delivery gun. This can minimize potential non-sterile contact with the plunger. According to one embodiment, a deflection shield, 430, can be used to angle the flexible plunger 500 away from a user's line of sight, body, or hand.

Referring to FIGS. 7 to 12, a bone graft delivery system 150 may be similar to the bone graft delivery system 100 as described above such that the description of the bone graft delivery system 100 is applicable to the bone graft delivery system 150, and vice versa unless expressly described to the contrary.

The bone graft delivery system 150 may include a delivery gun 450 (e.g., similar to the delivery gun 400) comprising a proximal end 452, a distal end 454, and a body 456 extending therebetween. The delivery gun 450 (e.g., the body 406) may include a tubular member that defines a lumen 458 extending through the body 456 from the proximal end 452 to the distal end 454. The delivery gun 450 may include a longitudinal axis 460 along which the lumen 458 extends from the proximal end 452 to the distal end 454.

The bone graft delivery system 150 may include a cannula 250 (e.g., similar to the cannula 200) couplable to the distal end 454 of the delivery gun 450. The cannula 250 may define a lumen 252 extending through a tubular body 254 of the cannula 250. As shown, the tubular body 254 and the lumen 252 may include a first portion 256 that extends along a first cannula axis 258, and may further include a second portion a second portion 260 that is offset (e.g., angularly offset) from the first portion 256. According to one embodiment, the second portion 260 may extend along a second cannula axis 262. Alternatively, one or both of the first portion 256 and the second portion 260 may be non-linear (e.g., curved).

When the cannula 250 is coupled to the delivery gun 450, the first cannula axis 258 may be colinear with the longitudinal axis 460, and the second cannula axis 262 may be angularly offset from the longitudinal axis 460 by an offset angle α. The offset angle α may be less than 180° and greater than about 90°, for example between about 100° and about 170°, such as about 110°. The offset angle α may be fixed (e.g., due to the stiffness of the cannula 250), or may be adjustable/variable. For example, the cannula 250 may be flexible so as to allow adjustment of the offset angle α. According to one embodiment, the cannula 250 may include a hinge (e.g., between the first portion 256 and the second portion 260) that is actuable to adjust the offset angle α.

Figure 8:
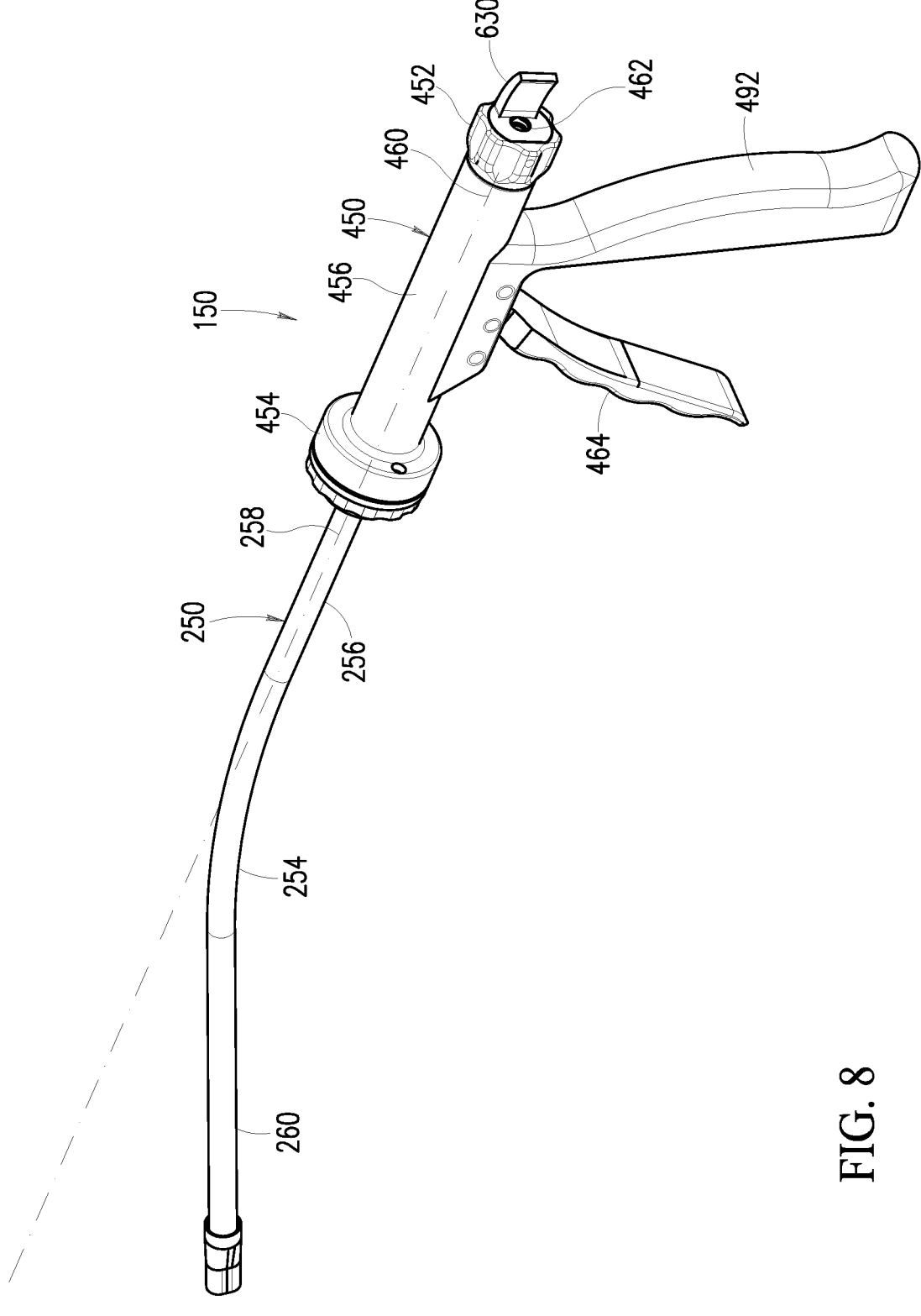
FIG. 8 is a rear isometric view of the bone graft delivery system illustrated in FIG. 7.

The bone graft delivery system 150 may include a plunger 550 (similar to the plunger 500, and also referred to herein as a "flexible plunger"). The plunger 550 may be sized to be insertable into the lumen 458 through an opening 462 defined by the proximal end 452. As shown in FIG. 8, the plunger 550 may be movable within the bone graft delivery system 150 to a position in which a proximal portion 552 of the plunger 550 is within the lumen 458 (e.g., between the proximal end 452 and the distal end 454, and a distal portion 554 of the plunger 550 is within the second portion 260 of the lumen 252 (e.g., such that the proximal portion 552 is angularly offset from the distal portion 554 by the offset angle α).

The bone graft delivery system 150 may further include a trigger 464, a first circumferential engagement mechanism 466, and a second circumferential engagement mechanism 468 (similar to the trigger 405, first circumferential engagement mechanism 413, and second circumferential engagement mechanism 414, respectively as described above). The trigger 464 is actuable to advance the first circumferential engagement mechanism 466, which in turn clamps on and advances the plunger 550 within the lumen 458 toward the distal end 454. When the trigger 464 is released, the second circumferential engagement mechanism 468 clamps on and prevents movement of the plunger 550 toward the proximal end 452.

According to one embodiment, the trigger 464 is coupled to body such that the trigger 464 is pivotable relative to the body 456 about a pivot axis 490 that is between the proximal end 452 and the distal end 454 with respect to a direction parallel to the longitudinal axis 460. The delivery gun 450 may further include a handle 492 (similar to the stationary handle 404) coupled to the body 456 such that the handle 492 is closer to the proximal end 452 than the trigger 464 is from the proximal end 452, and the trigger 464 is closer to the distal end 454 than the handle 492 is from the distal end 454.

The trigger 464 may be actuated/engaged by pivoting the trigger 464 about the pivot axis 490 toward the handle 492, and the trigger 464 may be disengaged by pivoting the trigger 464 about the pivot axis 490 away from the handle 492 (e.g., by releasing the trigger 464 and allowing a spring force to pivot the trigger 464).

Figure 7:
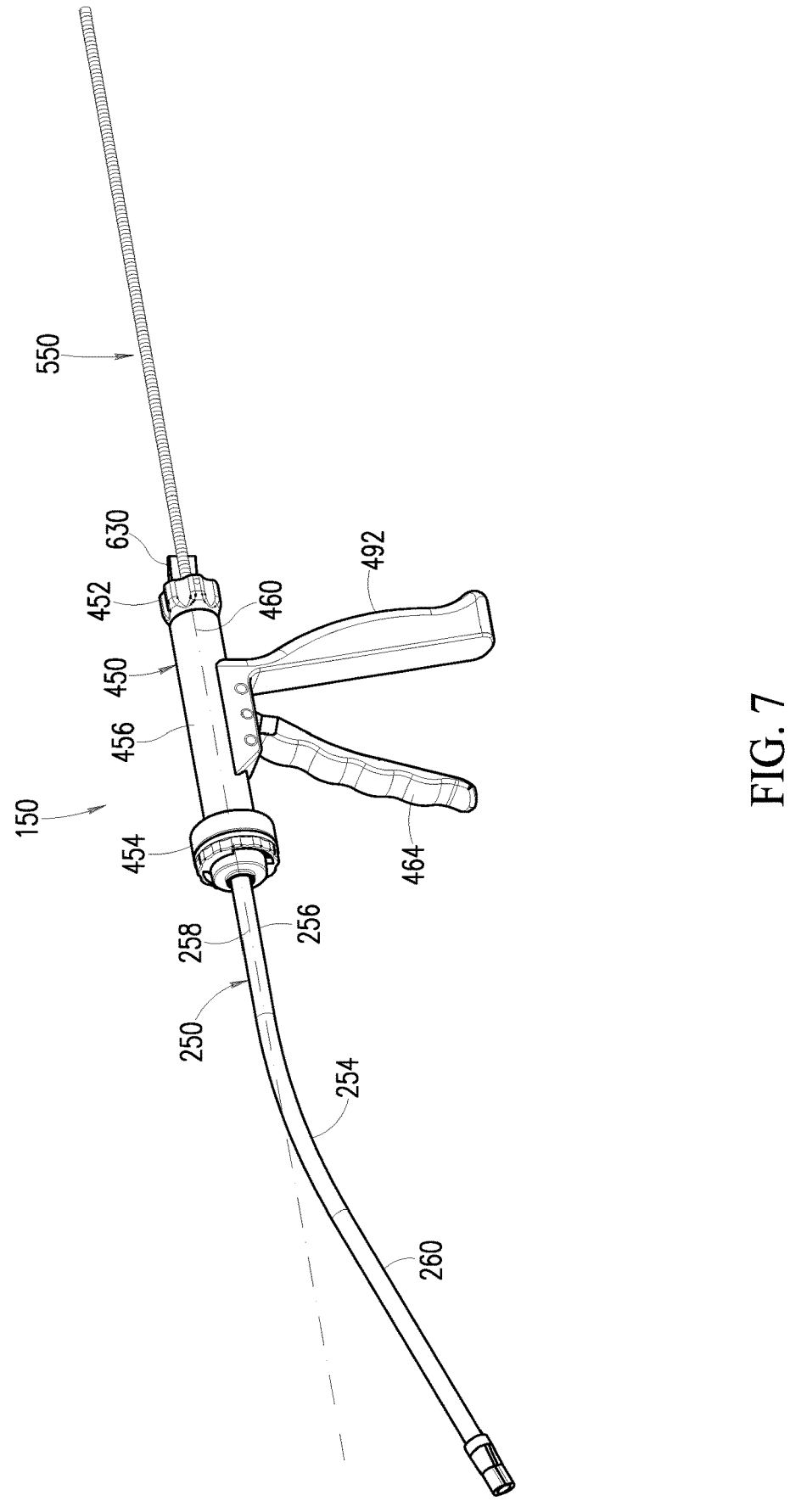
FIG. 7 is a front isometric view of a bone graft delivery system.
Figure 9:
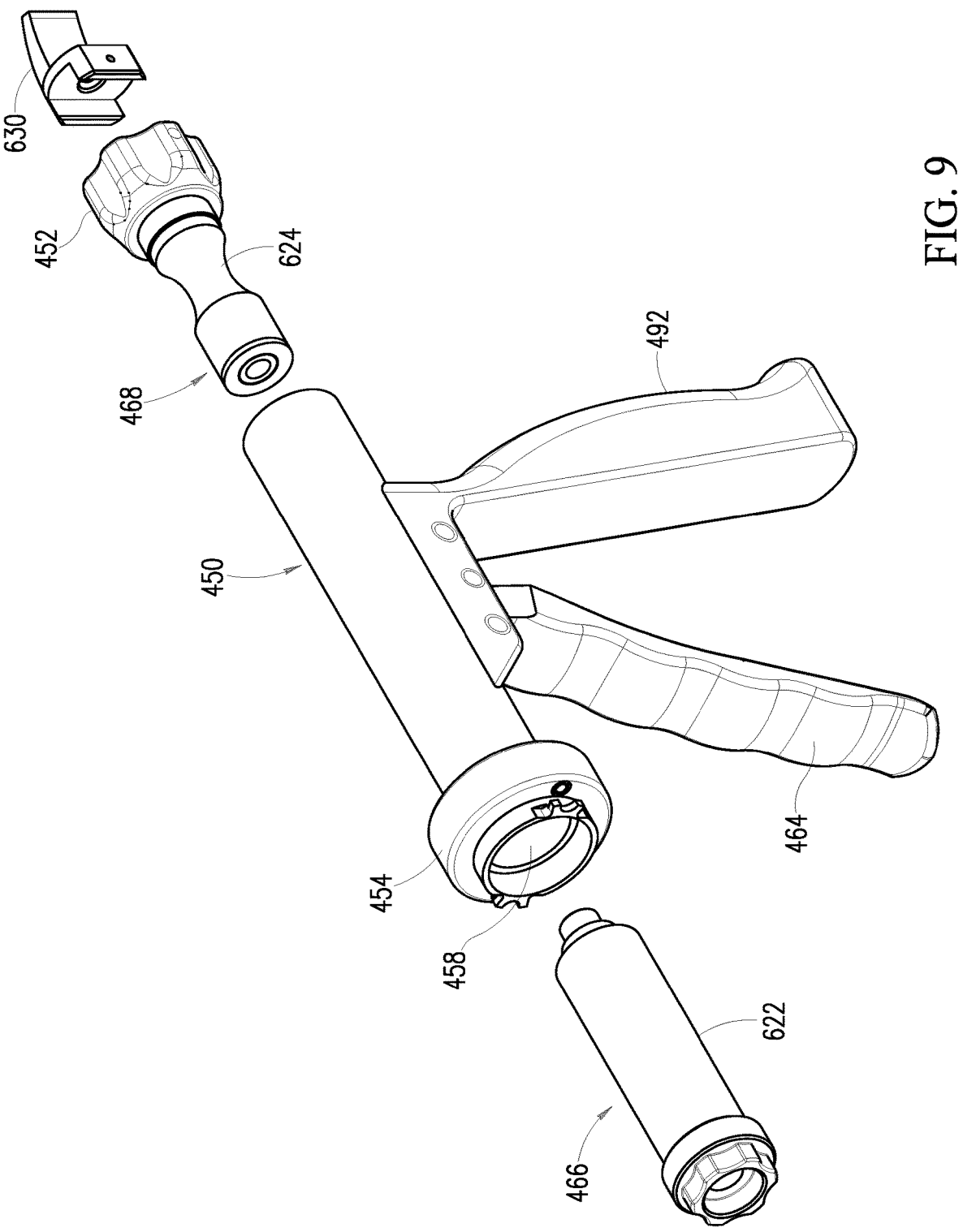
FIG. 9 is an exploded view of a delivery gun of the bone graft delivery system illustrated in FIG. 7.

The bone graft delivery system 150 may include an assembled configuration (e.g., as shown in FIGS. 7 and 8) in which the first circumferential engagement mechanism 466 and the second circumferential engagement mechanism 468 are positioned within the lumen 458. The bone graft delivery system 150 may include a disassembled configuration (e.g., as shown in FIG. 9) wherein the first circumferential engagement mechanism 466 and the second circumferential mechanism 468 are removed from the lumen 458. The bone graft delivery system 150 may be transitional between the assembled configuration and disassembled configuration without plastic deformation (e.g., to allow the bone graft delivery system 150 to be cleaned and sterilized after use).

As shown, the first circumferential engagement mechanism 466 may include a first split ring 602 with a first inner surface 604 that includes a plurality of teeth 606 that correspond to the plunger 550, and a first tapered outer surface 608. The first circumferential engagement mechanism 466 may further include a first spring 610 that exerts a first biasing force toward the first split ring 602 (e.g., directly or indirectly) and toward the proximal end 452. The second circumferential engagement mechanism 468 may include a second split ring 612 with a second inner surface 614 that includes a plurality of teeth 616 that correspond to the plunger 550, and a second tapered outer surface 618. The second circumferential engagement mechanism 468 may further include a second spring 620 that exerts a second biasing force toward the second split ring 612 (e.g., directly or indirectly) and toward the proximal end 452.

The first and second circumferential engagement mechanisms 466 and 468 may be replaced with other engagement/advancement mechanisms that advance the plunger 550 through the lumen 458 and into the cannula 250. For example, the plunger 550 may be advanced by rotation and engagement of corresponding threads.

The bone graft delivery system 150 may include a housing (e.g., in the form of a first tubular member 622) that encloses the first circumferential engagement mechanism 466 (e.g., the first split ring 602 and the first spring 610), and a housing (e.g., in the form of a second tubular member 624) that encloses the second circumferential engagement mechanism 468 (e.g., the second split ring 612 and the second spring 620). The first tubular member 622 with the first split ring 602 and the first spring 610 enclosed therein may be removable from the lumen 458 (e.g., via disengagement of corresponding threads). Similarly, the second tubular member 624 with the second split ring 612 and the second spring 620 enclosed therein may be removable from the lumen 458 (e.g., via disengagement of corresponding threads). Insertion/removal of the first and second tubular members 622 and 624 may transition the bone graft delivery system 150 from the assembled configuration to the disassembled configuration, and vice versa.

The bone graft delivery system 150 may further include a deflector 630 (e.g., similar to the deflector shield 430) coupled to the proximal end 452 of the delivery gun 450 and positioned so as to deflect a portion 556 of the plunger 550 that extends proximally from the proximal end 452 away from the longitudinal axis 460.

Referring to FIGS. 13 to 20, the cannula 250 may be detachable from the delivery gun 450 (e.g., regardless of whether the plunger 500 is within the lumen 252 and/or the lumen 458). For example, the cannula 250 may be detachable from the delivery gun 450 when the plunger 500 is at the position without removing the proximal portion 552 of the plunger 500 from the lumen 458.

The cannula 250 may include a proximal end 264 that is couplable to the distal end 454 of the delivery gun 450. The cannula 250 (e.g., the tubular body 254 may extend to and terminate at a distal tip 266. According to one embodiment, the first portion 256 may be closer to the proximal end 264, and the second portion 260 may be closer to the distal tip 266. As shown, the distal tip 266 may define have an oval shaped outer perimeter 268 that corresponds to an access window into the delivery location for the bone graft material (e.g., an intervertebral disc space). The lumen 458 may have a circular cross-sectional shape and a cross-sectional area that remains constant from the proximal end 264 to the distal tip 266.

The cannula 250 and the delivery gun 450 may be couplable by engaging corresponding features of a connector 270 of one of the cannula 250 and the delivery gun 450 with corresponding features of a hub 470 of the other of the cannula 250 and the delivery gun 450. As shown in the illustrated embodiment, the cannula 250 includes the connector 270 and the delivery gun 450 includes the hub 470, however according to another embodiment, the connector 270 and hub 470 could be reversed.

Figure 10:
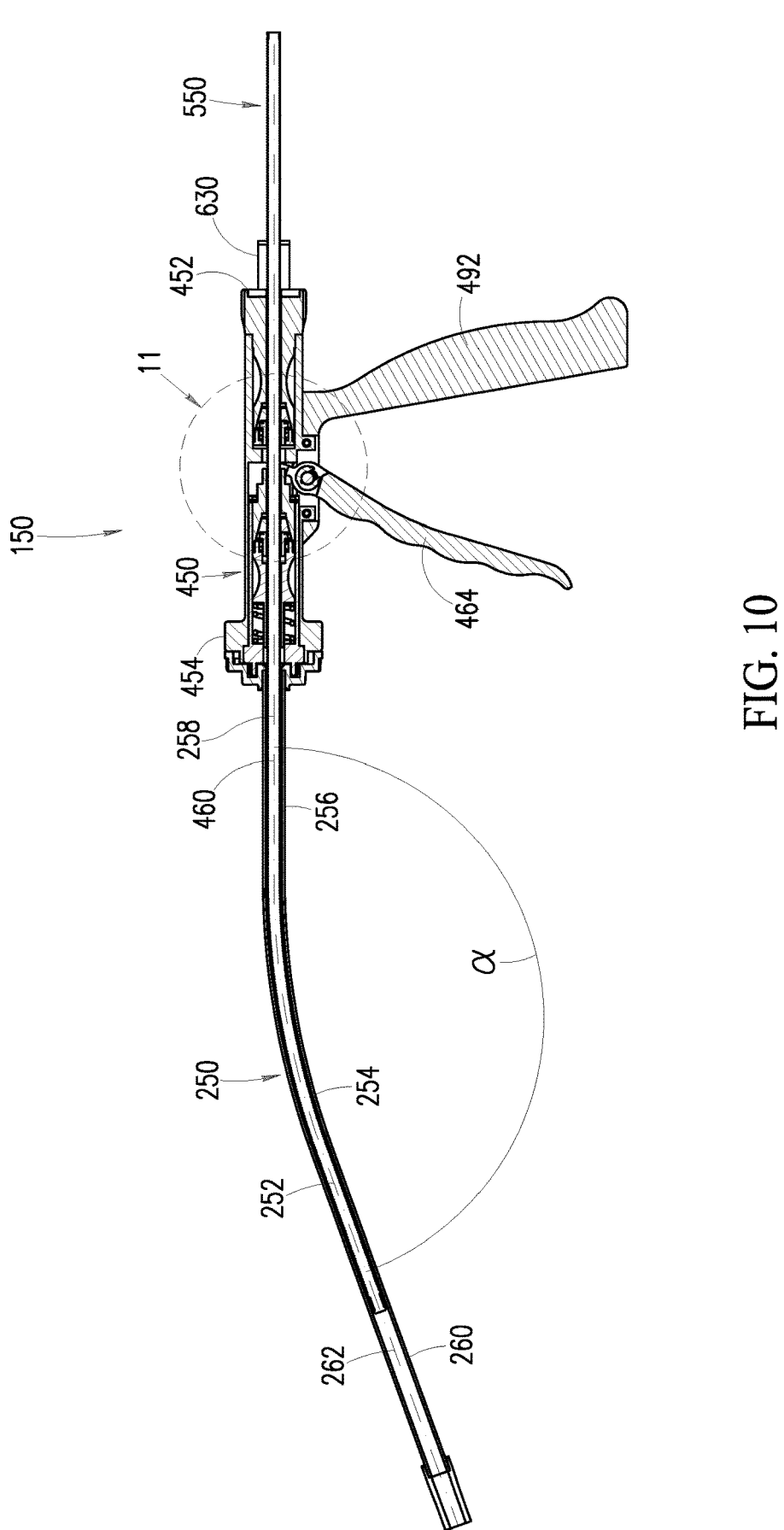
FIG. 10 is a cross-sectional view of the bone graft delivery system illustrated in FIG. 7.
Figure 11:
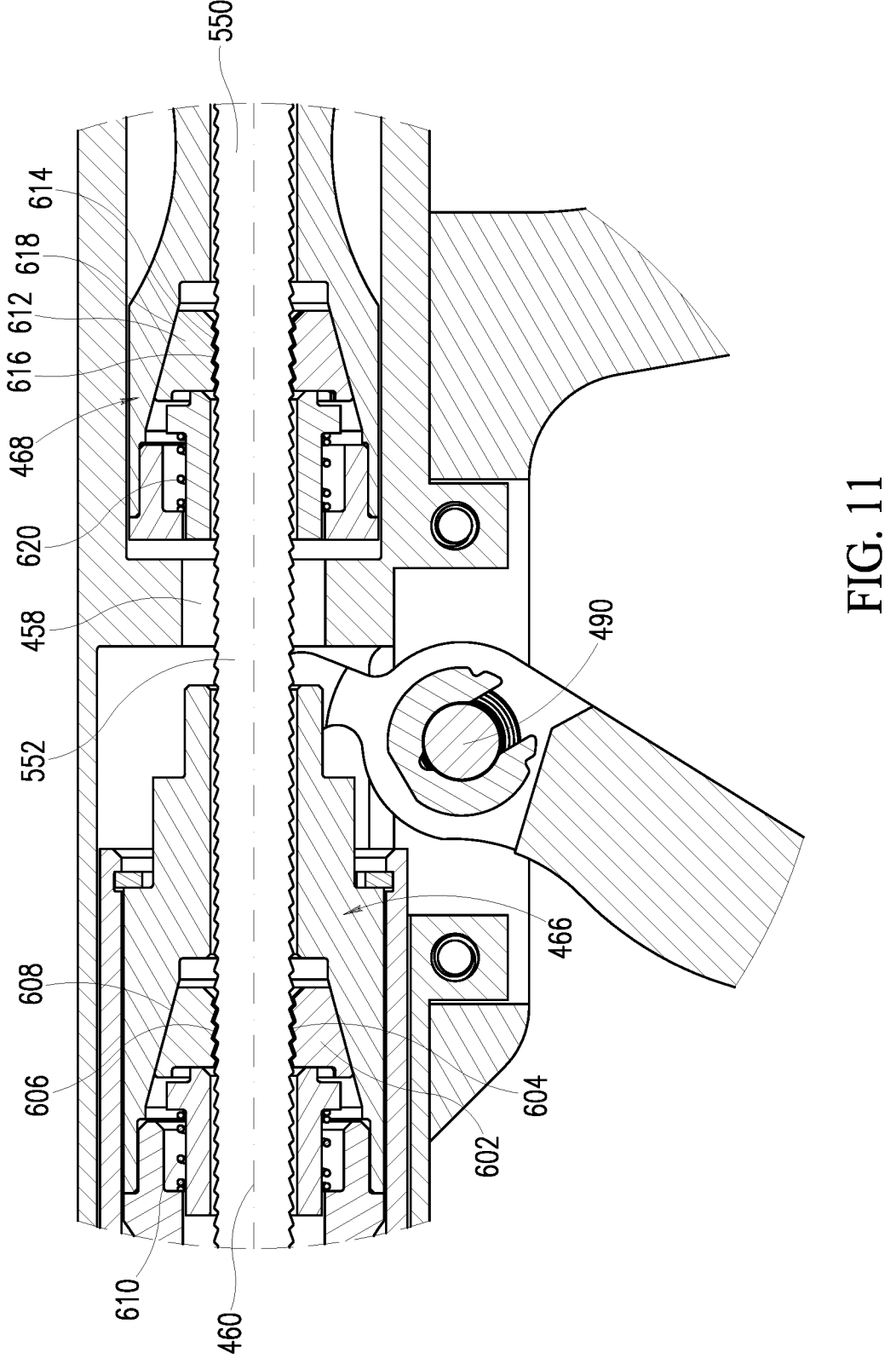
FIG. 11 is an enlarged view of a portion of the delivery gun of the bone graft delivery system illustrated in FIG. 10.
Figure 12:
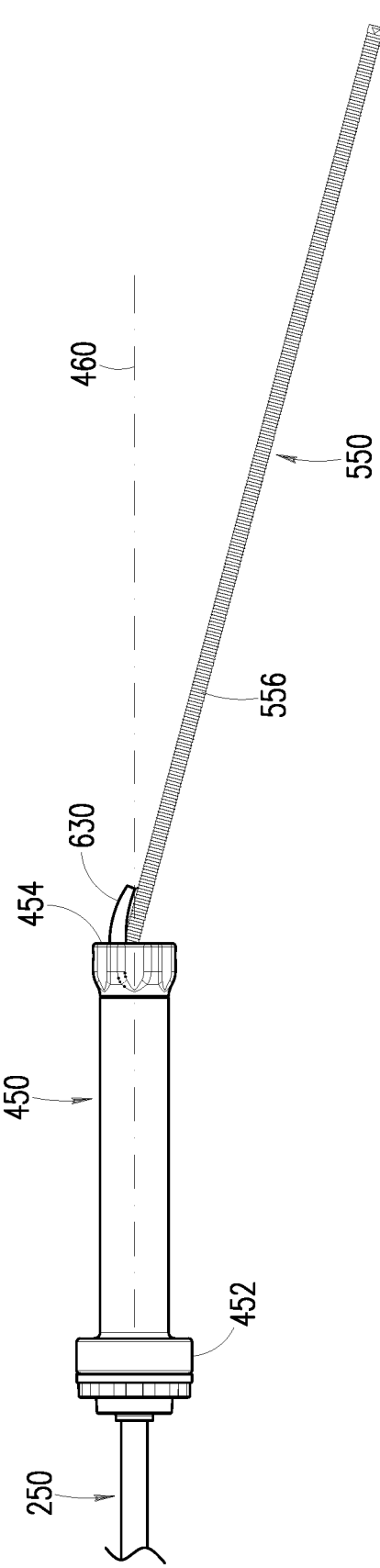
FIG. 12 is a top plan view of the bone graft delivery system illustrated in FIG. 7.
Figures 13, 14:
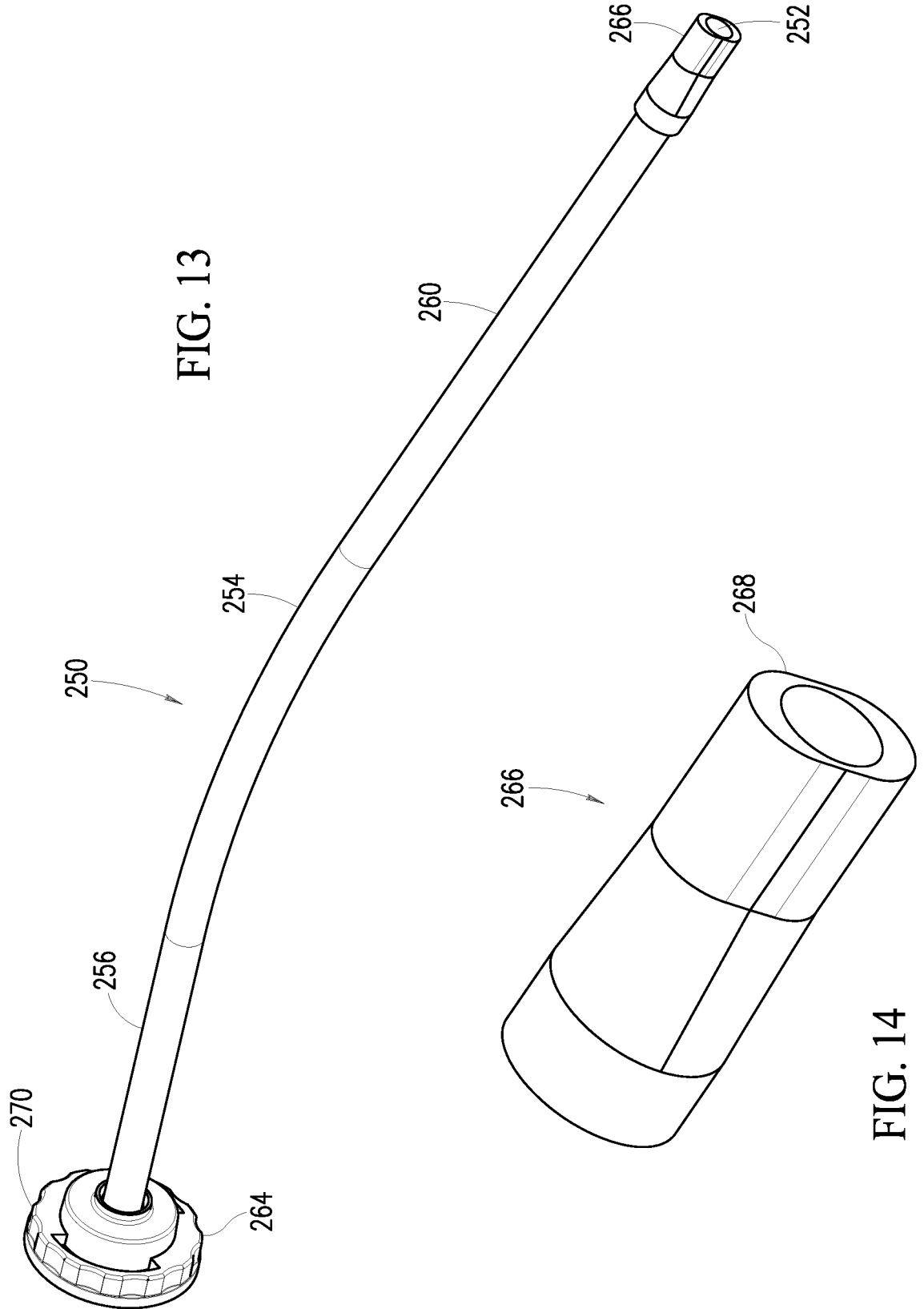
FIG. 13 is an isometric view of a cannula of the bone graft delivery system illustrated in FIG. 7.
FIG. 14 is an isometric view of a distal tip of the cannula illustrated in FIG. 13.
Figures 15, 16, 17:
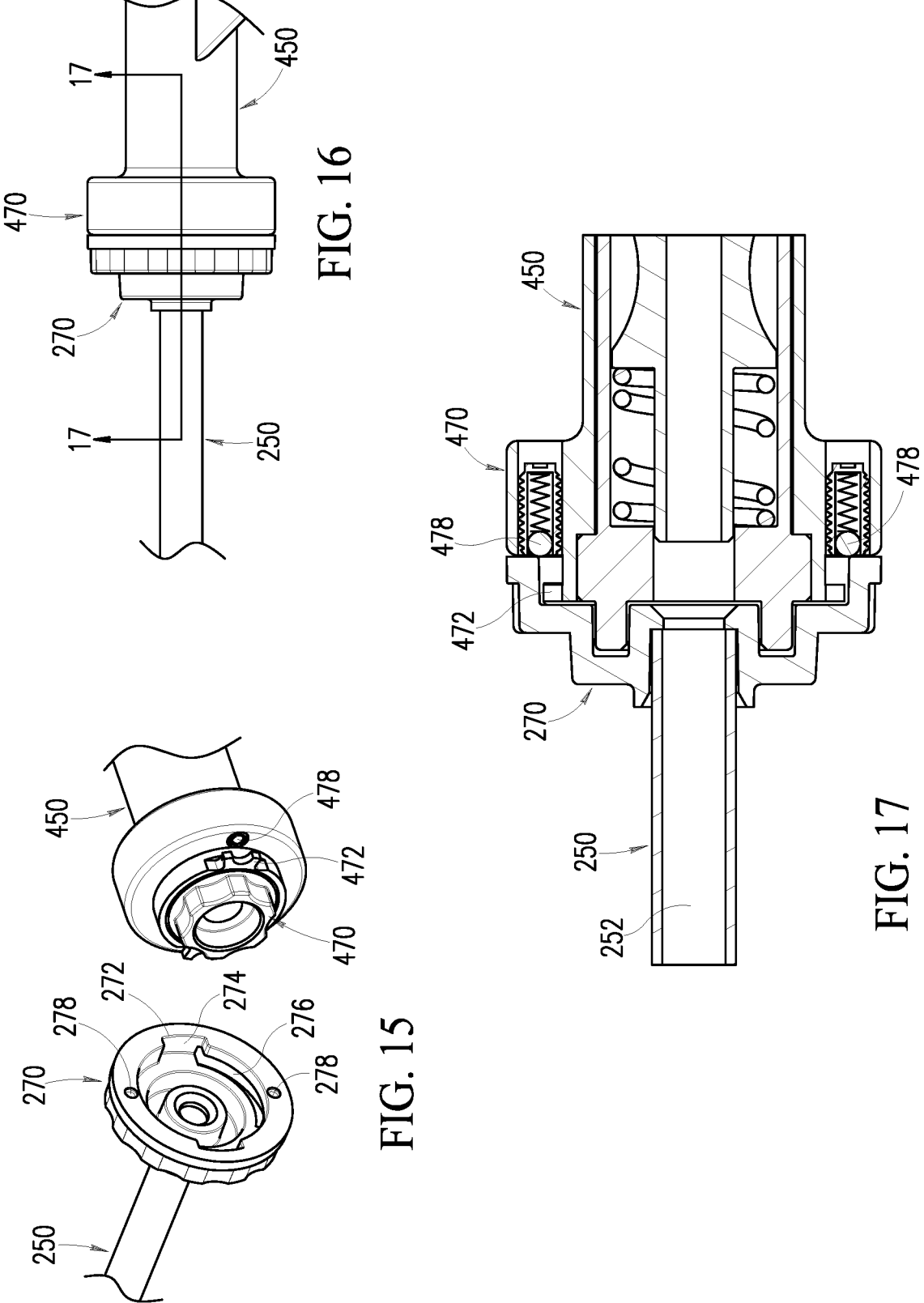
FIG. 15 is an isometric view of engagement features of the cannula and the delivery gun of the bone graft delivery system illustrated in FIG. 7, in a first orientation.
FIG. 16 is a side elevation view of the engagement features of the cannula and the delivery gun illustrated in FIG. 15.
FIG. 17 is a cross-sectional view of the engagement features of the cannula and the delivery gun illustrated in FIG. 15.

The corresponding features may be engageable to couple the cannula 250 to the delivery gun 400 in a plurality of orientations. For example, the corresponding features may be engageable to couple the cannula 250 to the delivery gun 400 such that the distal tip 266 is offset in a "downward" direction (as shown in FIG. 10), but may also be engageable such that the distal tip 266 is offset in an "upward" direction (e.g., radially opposite the "downward" direction), a "leftward" direction (e.g., radially offset from the "downward" direction by 90°), and a "rightward" direction (e.g., radially opposite the "leftward" direction).

According to one embodiment, the corresponding features include at least one track 272 carried by one of the connector 270 or the hub 470, and at least one follower 472 carried by the other of the connector 270 or the hub 470. The follower(s) 472 may each be sized to fit within and ride along a respective one of the track(s) 272. Engaging the track(s) 272 and the follower(s) 472 may include a push-and-rotate motion (e.g., of the cannula 250 relative to the delivery gun 450). For example, the track(s) 272 may include a first portion 274 extending into the connector 270 along a first direction, and a second portion 276 extending into the connector 270 along a second direction that lies within a plane that is normal to the first direction.

The corresponding features may include a lock that provides resistance to removal/decoupling of the cannula 250 and the delivery gun 450 (e.g., via removal of the follower 472 from the track 272). For example, the lock may include a spring biased member 478 and a recess 278 sized to receive at least a portion of the spring biased member 478. As shown, one of the connector 270 and the hub 470 may include the spring biased member(s) 478, and the other of the connector 270 and the hub 470 may include the recess(es) 278.

Figures 18, 19, 20:
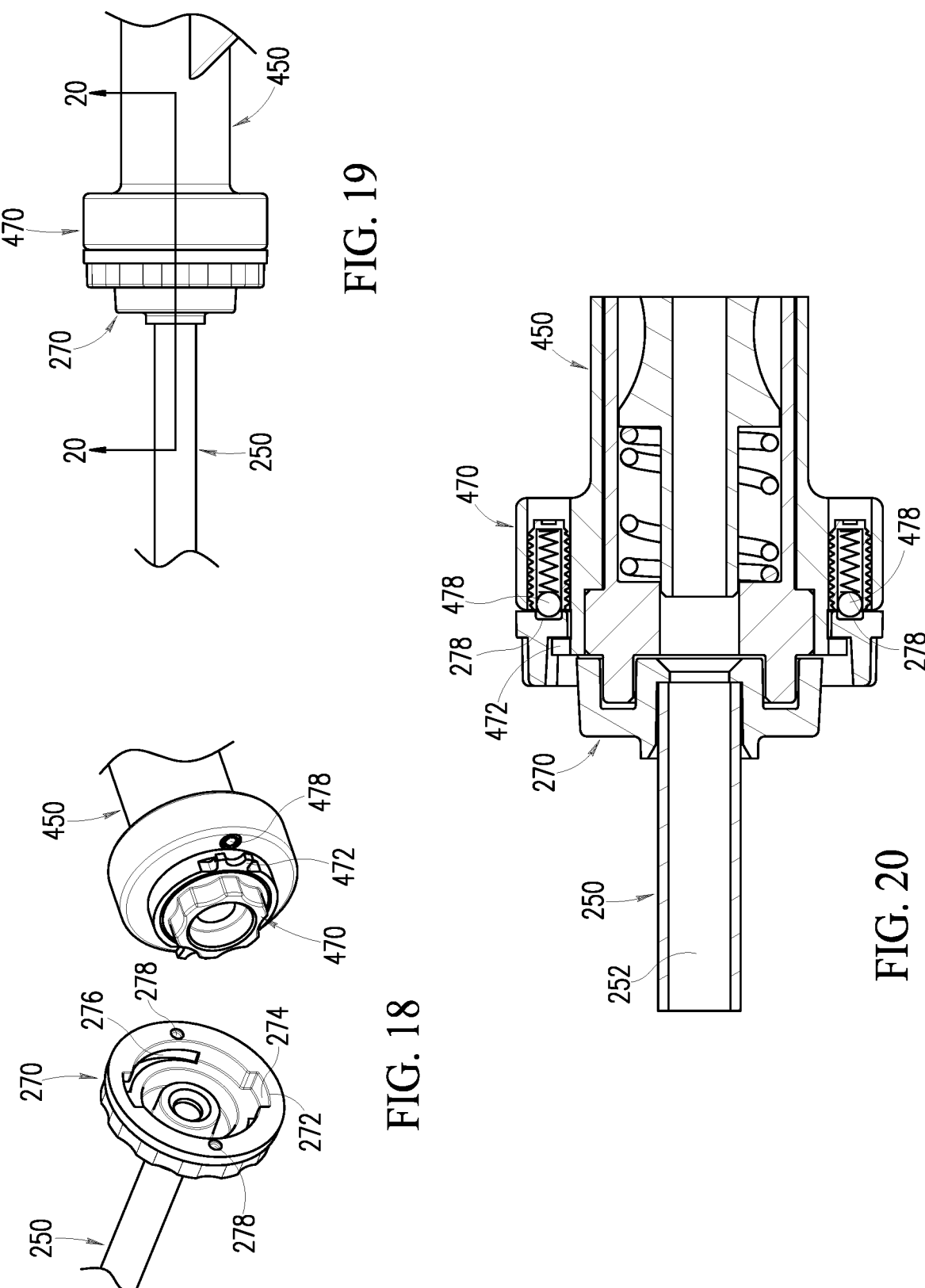
FIG. 18 is an isometric view of engagement features of the cannula and the delivery gun of the bone graft delivery system illustrated in FIG. 7, in a second orientation.
FIG. 19 is a side elevation view of the engagement features of the cannula and the delivery gun illustrated in FIG. 18.
FIG. 20 is a cross-sectional view of the engagement features of the cannula and the delivery gun illustrated in FIG. 18.
Figure 21:
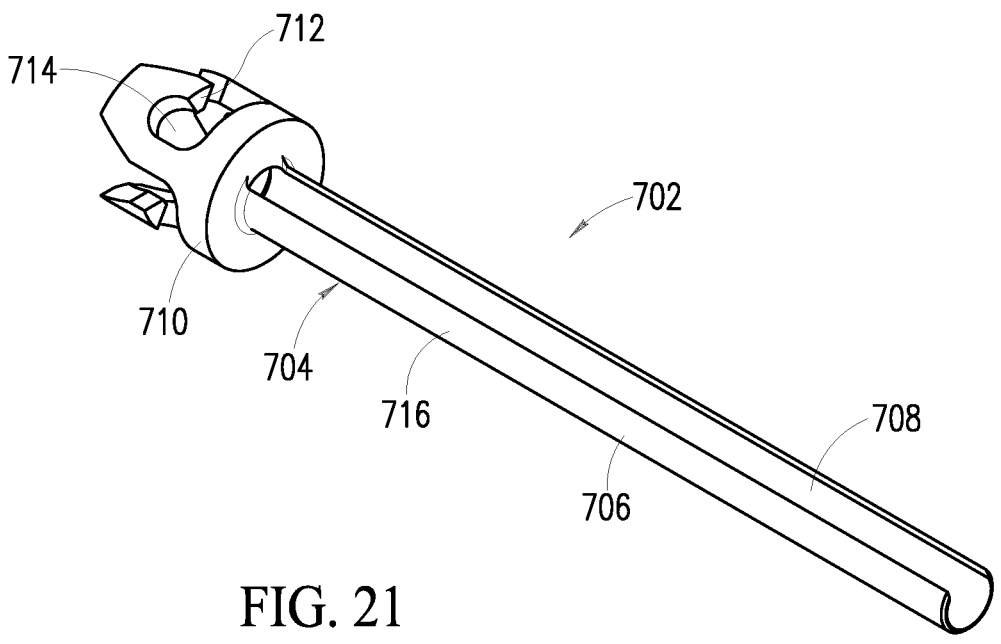
FIG. 21 is a front isometric view of a sled of a bone graft loader.
Figure 22:
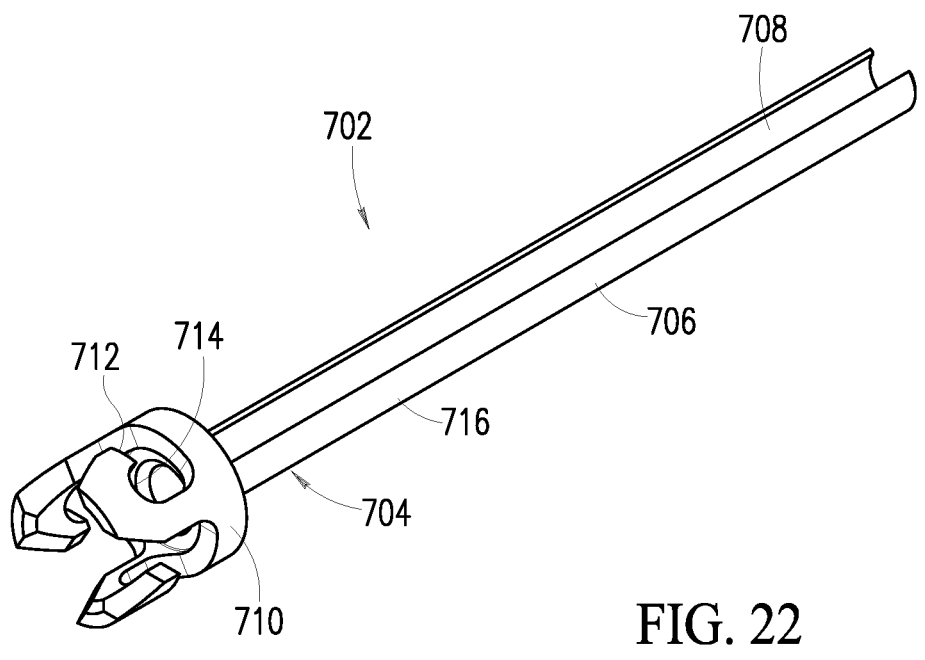
FIG. 22 is a rear isometric view of the sled illustrated in FIG. 21.
Figure 23:
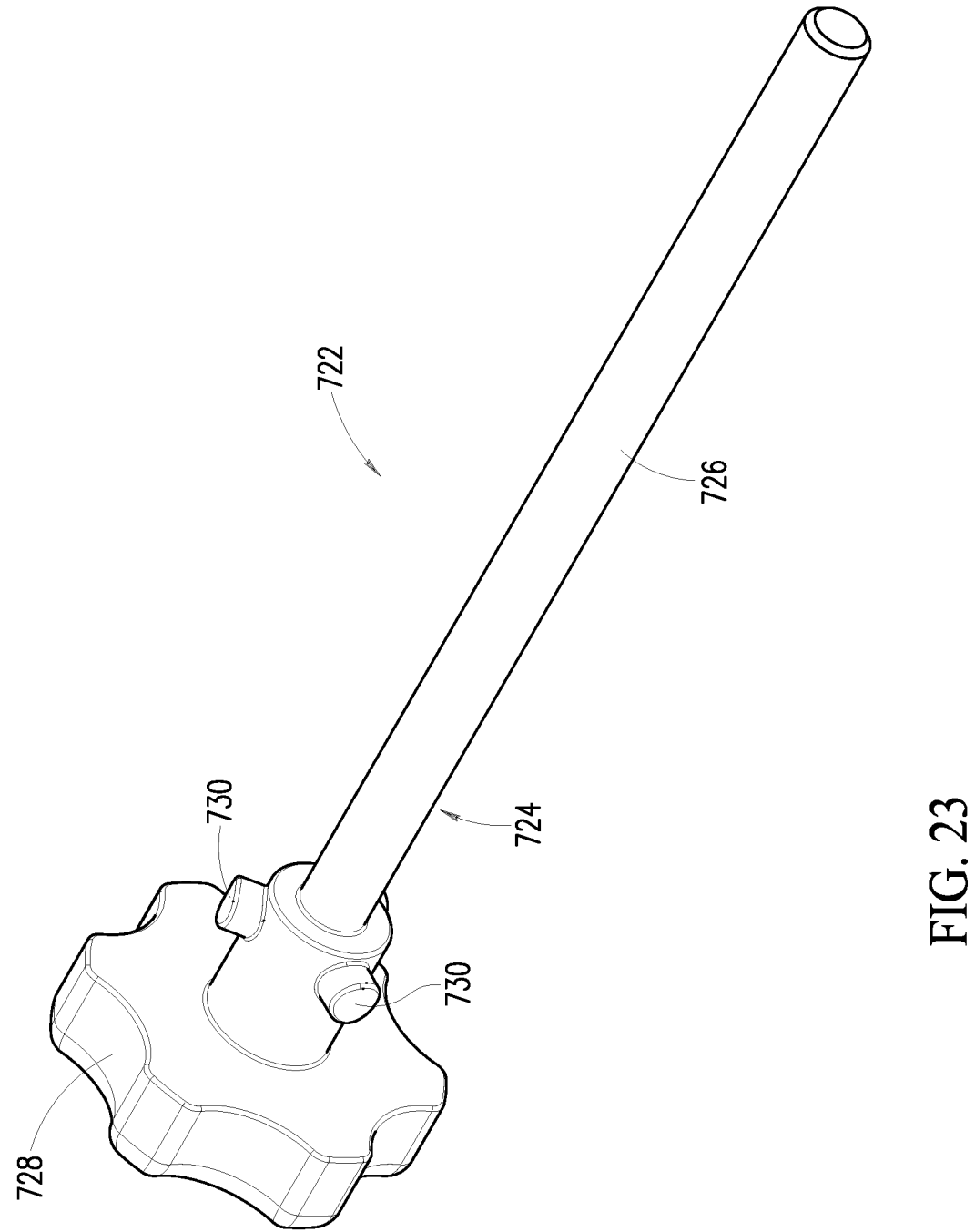
FIG. 23 is a front isometric view of a push rod of a bone graft loader.
Figure 24:
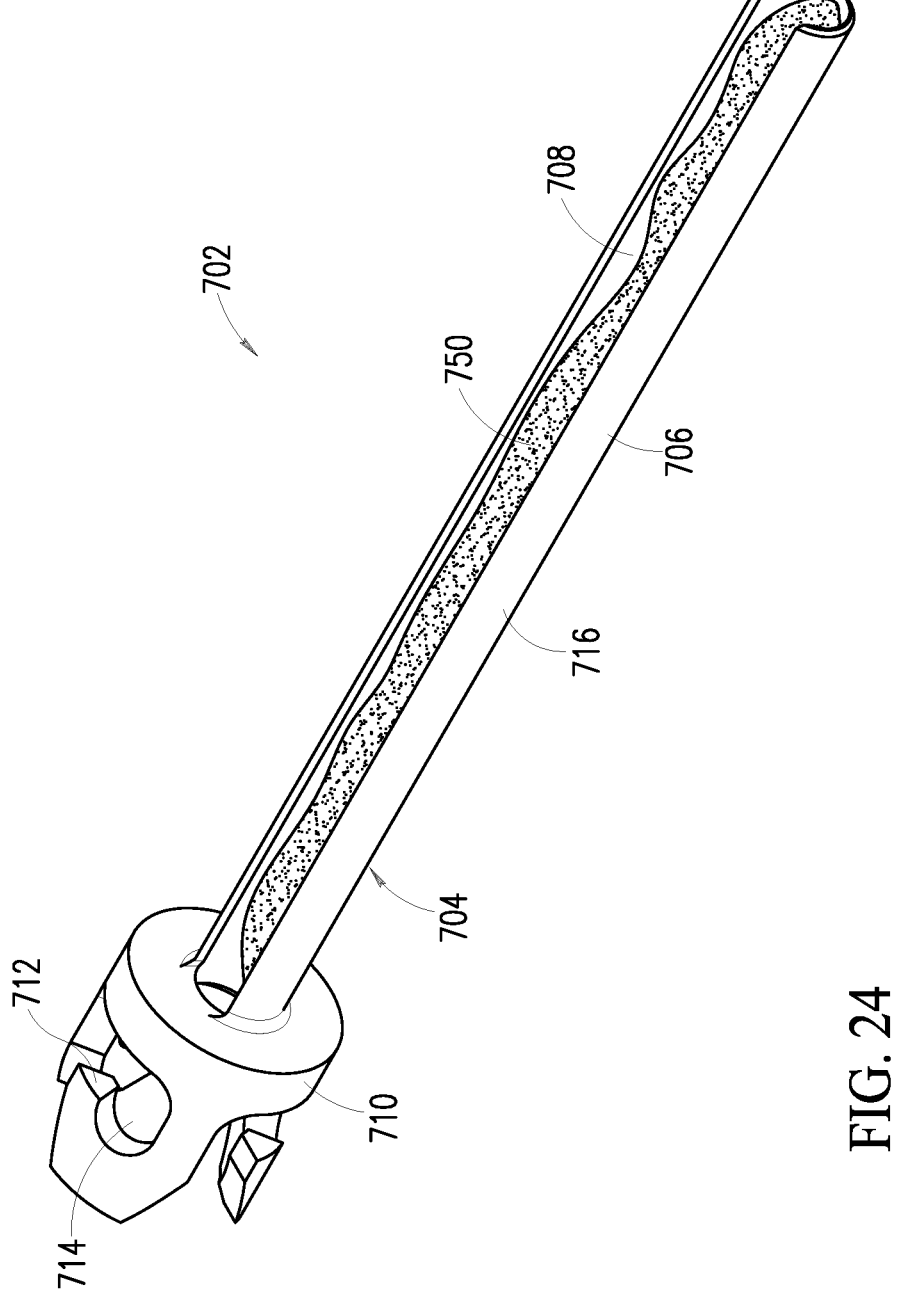
FIG. 24 is a front isometric view of the sled illustrated in FIG. 21 loaded with bone graft material.
Figure 25:
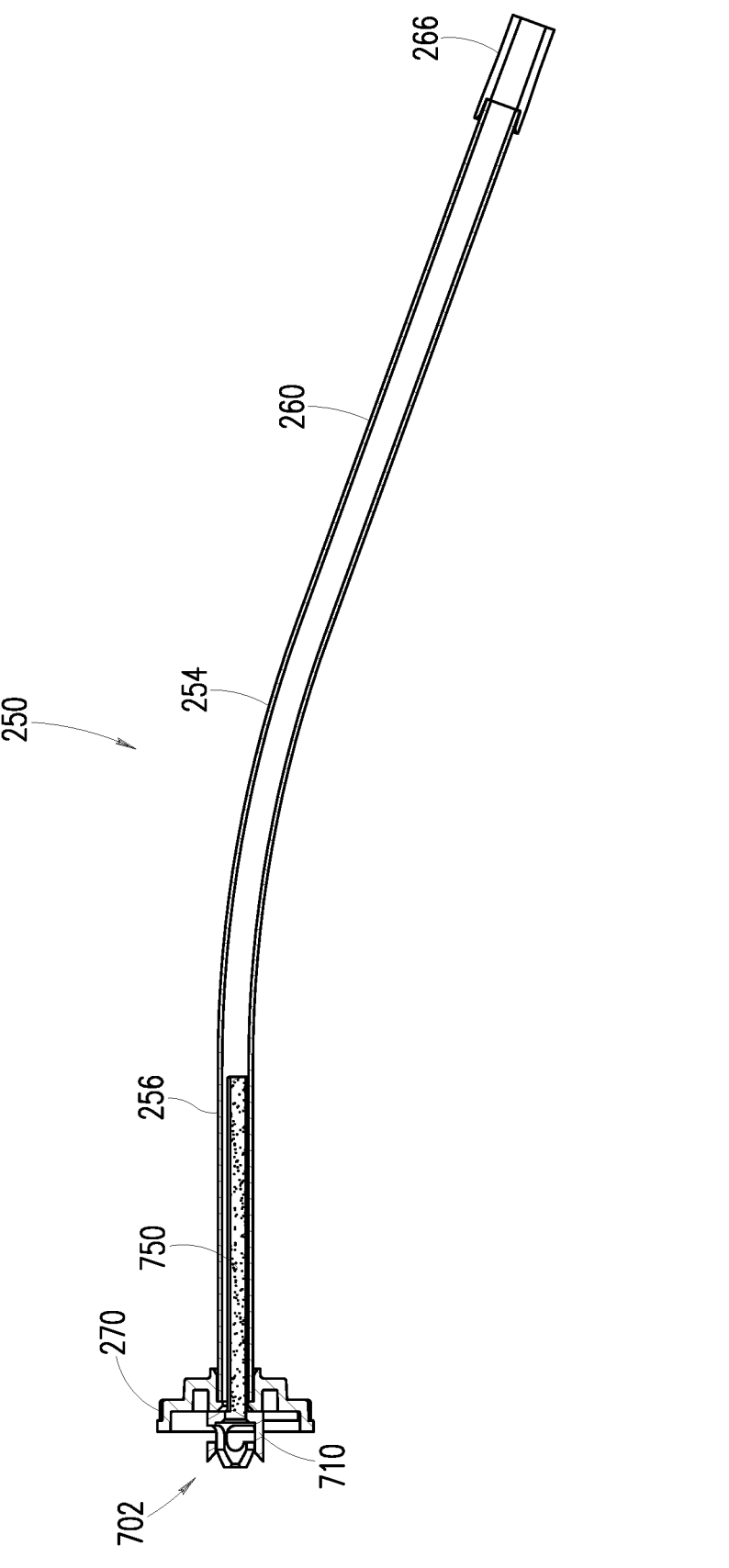
FIG. 25 is a cross-sectional view of the sled illustrated in FIG. 21 in use to load the bone graft material into the cannula illustrated in FIG. 13.
Figure 26:
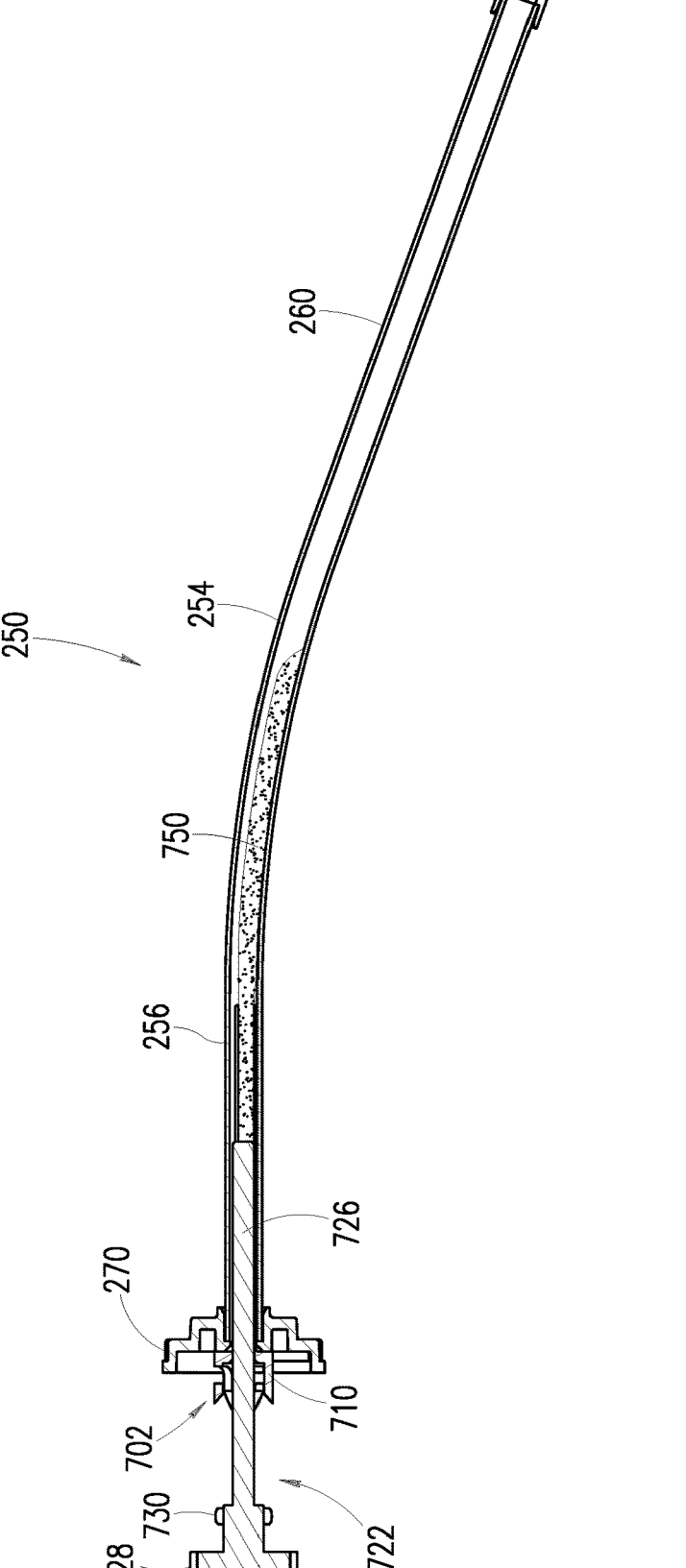
FIG. 26 is a cross-sectional view of the sled illustrated in FIG. 21 and the push rod illustrated in FIG. 23 in use to load the bone graft material into the cannula illustrated in FIG. 13.
Figure 27:
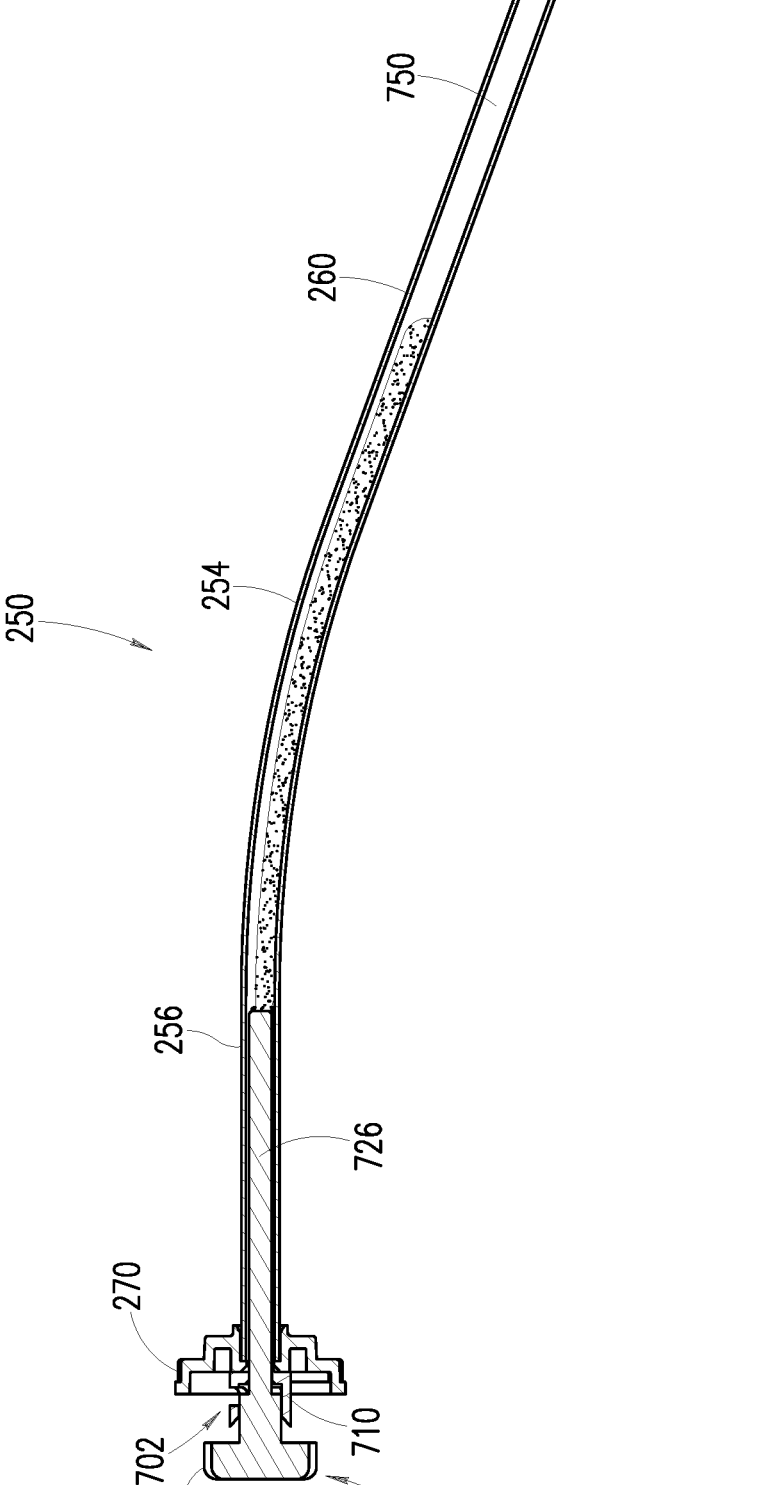
FIG. 27 is a cross-sectional view of the sled, push rod, and cannula illustrated in FIG. 26, at another phase in the loading process.
Figure 28:
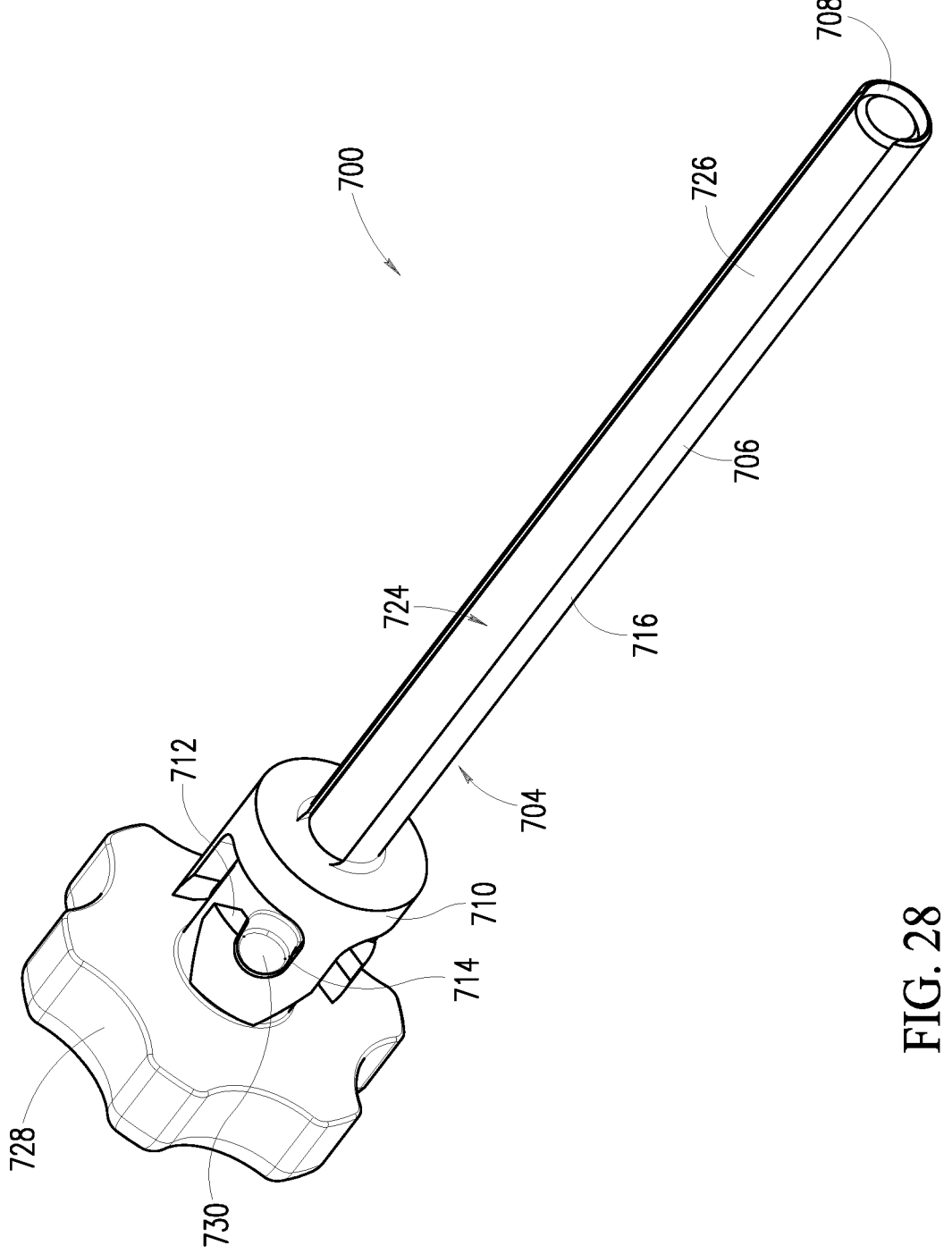
FIG. 28 is a front isometric view of the bone graft loader including the push rod illustrated in FIG. 23 engaged with the sled illustrated in FIG. 21.

As shown in FIG. 20, when the follower 472 reaches an end of the track 272 (e.g., after completing the push-and-rotate movement, after moving through both the first portion 274 and the second portion 276, etc.) the recess 278 may be aligned with the spring biased member 478. When aligned, at least a portion of the spring biased member 478 enters the recess 278, thereby resisting relative rotation of the cannula 250 and the delivery gun 450. The resistance to relative to rotation may be overcome by enough torque being applied by a user of the bone graft delivery system 150.

Referring to FIGS. 21 to 28 a bone graft loader 700 may include a sled 702 having an elongate body 704. The elongate body 704 may include a tubular member 706 defining a channel 708 extending therethrough. The elongate body 704 may further include a collar 710 extending from the tubular member 706. As shown, the collar 710 may define a collar track 712 extending into the collar and toward the tubular member 706. According to one embodiment, the collar track 712 may include a non-linear portion 714. As shown, the collar track 712 may have a hook or "J" shape. According to one embodiment, the tubular member 706 of the sled 702 includes a trough 716 with an open cross-sectional shape/perimeter such that the channel 708 is accessible along a length of the trough 716.

The bone graft loader 700 may further include a push rod 722 having an elongate body 724 with a rod portion 726 shaped to correspond to the channel 708 such that the rod portion 726 is slidable within the channel 708 (e.g., to push bone graft material along the channel 708 as the rod portion 726 slides along the channel 708). The elongate body 724 of the push rod 722 may further include a handle 728 extending from the rod portion 726, and a projection 730 shaped to fit within and follow along the collar track 712, including the non-linear portion 714 of the collar track 712. According to one embodiment, the projection 730 may be located between the handle 728 and the rod portion 726.

The collar track 712 may be one of a plurality of collar tracks 712 spaced circumferentially about the sled 702 (e.g., the collar 710), and the projection 730 may similarly be one of a plurality of projections 730 spaced circumferentially about the push rod 722. According to one embodiment, the plurality of collar tracks 712 may be spaced circumferentially about the collar 710 equidistant from adjacent ones of the plurality of collar tracks 712, and the plurality of projections 730 may be similarly spaced circumferentially about the push rod 722 equidistant from adjacent ones of the plurality of projections 730.

The bone graft loader 700, and components thereof, may be used separately from or as a part of the bone graft delivery system 150. Accordingly, one embodiment of the bone graft delivery system 150 includes the bone graft loader 700, and an embodiment of the bone graft loader 700 may be made, sold, and/or used independently from a bone graft delivery system (e.g., the bone graft delivery system 150).

Referring to FIGS. 8 to 28, a method of delivering bone graft material may include loading bone graft material 750 into the lumen 252 of the cannula 250. The method may further include moving the distal portion 554 of the plunger 550 through the opening 462 formed in the proximal end 452 of the delivery gun 450, and then moving the distal portion 554 of the plunger 550 through the lumen 458 of the delivery gun 450, toward the distal end 454 of the delivery gun 450, along the longitudinal axis 460.

The method may further include moving the distal portion 554 of the plunger 550 through the distal end 454 and into the lumen 252 of the cannula 250. The distal portion 554 may then be moved into and through the first portion 256 of the cannula 250 (e.g., along the first cannula axis 258, which may be colinear with the longitudinal axis 460). The distal portion 554 may then be moved through the second portion 260 of the cannula 220 (e.g., along a direction that is angularly offset from first cannula axis 258 and the longitudinal axis 460, such as along the second cannula axis 262).

The method may further include pushing the loaded bone graft material 750 out of the lumen 252 of the cannula 250 with the distal portion 554 of the plunger 550 (e.g., via the distal tip 266). According to one embodiment, moving the bone graft material 750 through the lumen 252 of the cannula 250 may include moving the bone graft material 750 along a path that includes a non-linear portion (e.g., located between the first portion 256 and the second portion 260). The method may include loading the bone graft material 750 into the channel 708 of the sled 702, and then inserting the sled 702 into the lumen 252 of the cannula 250 such that the bone graft material 750 is positioned within the channel 708 and within the lumen 252 of the cannula 250.

The push rod 722 may then be moved into and along the channel 708 thereby pushing the bone graft material 750 out of the channel 708 and loading the bone graft material 750 into the lumen 252 of the cannula 250. The method may include inserting the projection 730 into the collar track 712, moving the projection 730 along the non-linear portion 714, and then exerting a force on the handle 728 thereby simultaneously removing the push rod 722 and the sled 702 from the lumen 252 of the cannula 250 without removing the push rod 722 from the channel 708 of the sled 702.

According to one embodiment, the sled 702 may be inserted into the lumen 252 of the cannula 250 through an opening 280 with a circular cross-sectional shape formed in the proximal end 264 of the cannula 250, and the loaded bone graft material 750 may be pushed out of the lumen 252 of the cannula 250 through an opening 282 formed in the distal tip 266 of the cannula 250. The openings 280 and 282 may have the same cross-sectional shape and/or cross-sectional area (e.g., to avoid necking or backpressure forming when the bone graft material 750 moves through cannula 250).

The method may include attaching the cannula 250 with the loaded bone graft material 750 inside the lumen 252 of the cannula 250 to the distal end 454 of the delivery gun 450. To attach the cannula to the delivery gun 450, the method may include rotating the cannula 250 with the loaded bone graft material 750 inside the lumen 252 of the cannula 250 relative to the delivery gun 450 (e.g., about the longitudinal axis 460).

Figure 29:
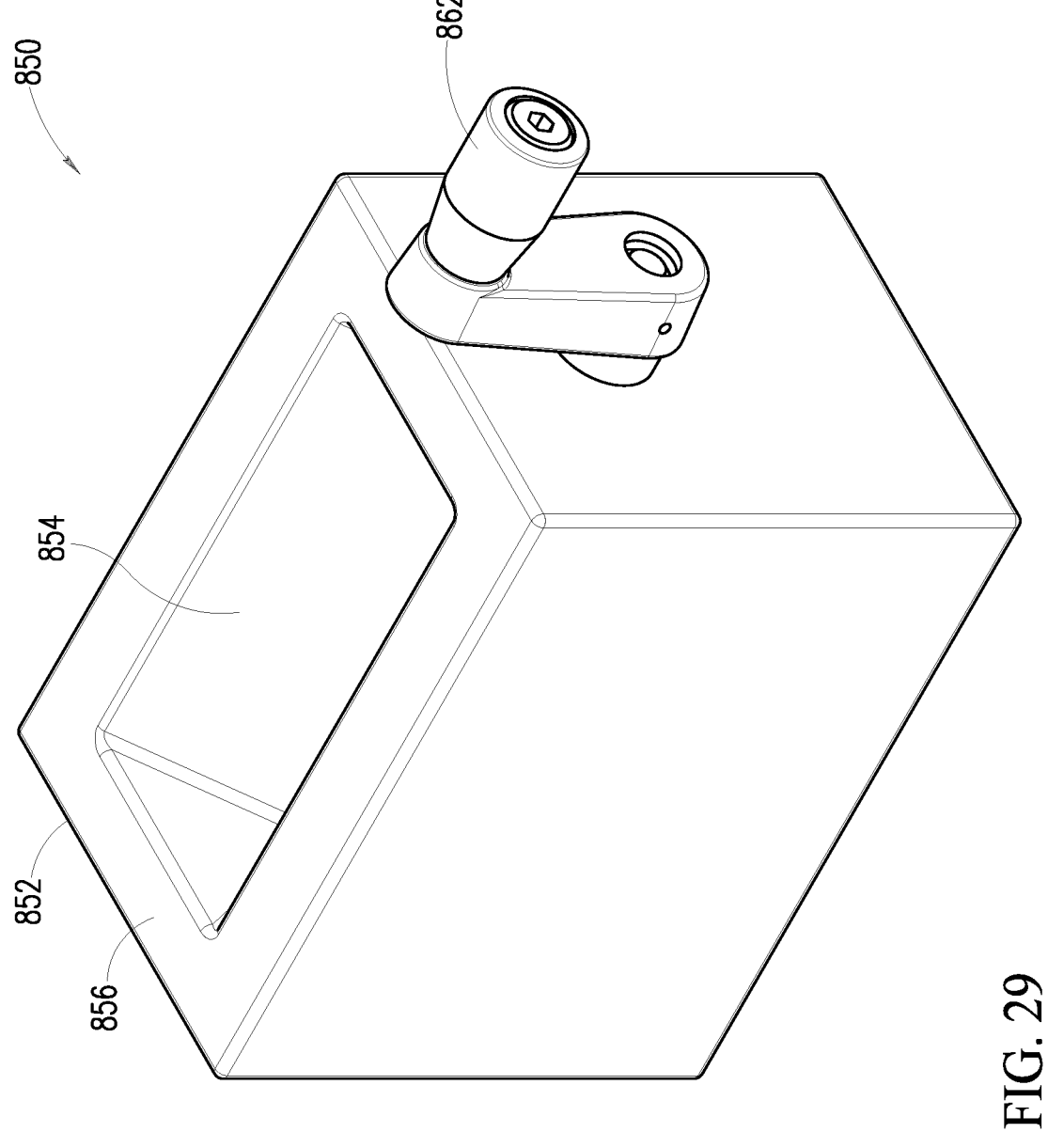
FIG. 29 is a front isometric view of a bone graft loader.
Figure 30:
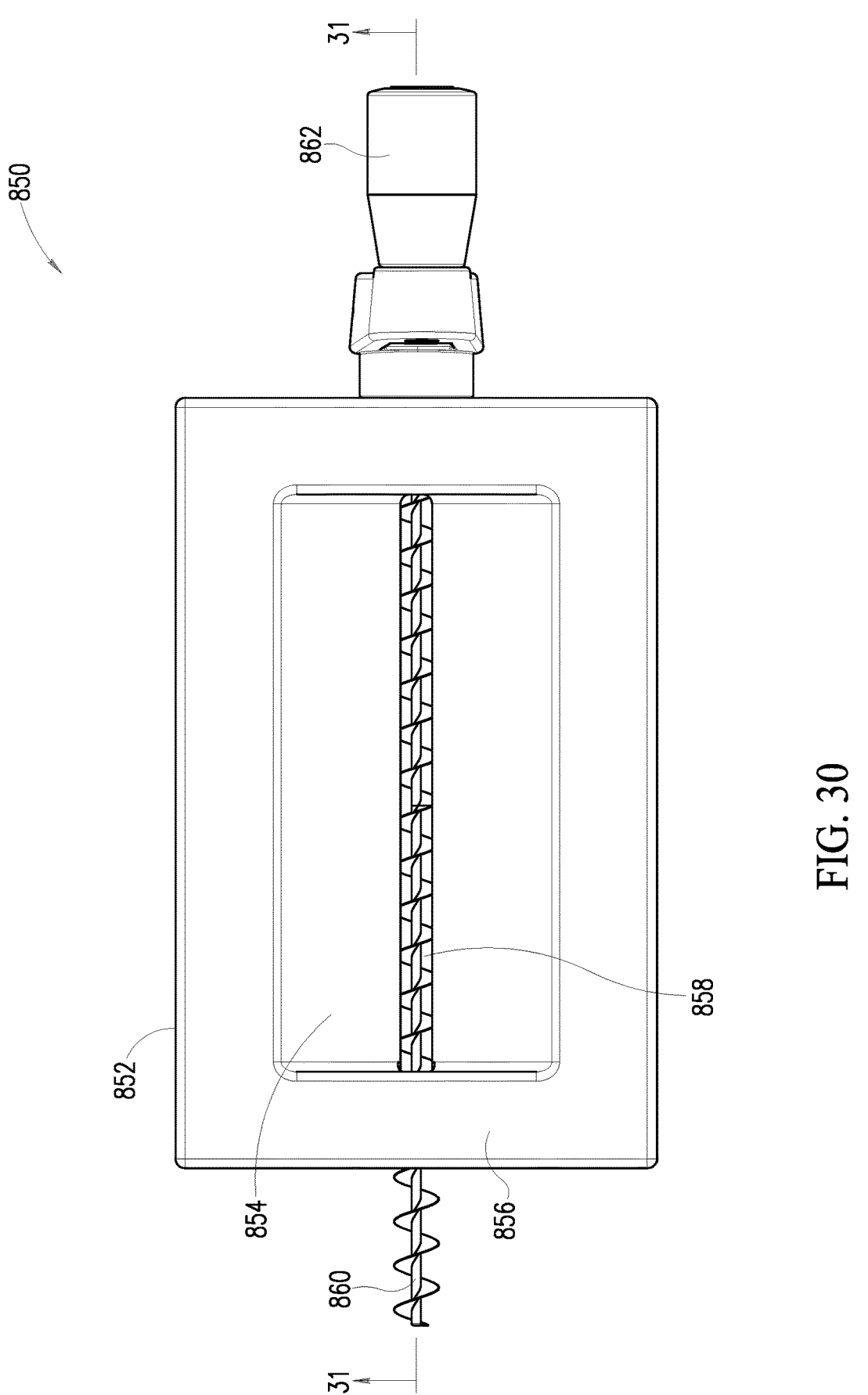
FIG. 30 is a top plan view of the bone graft loader illustrated in FIG. 29.
Figure 31:
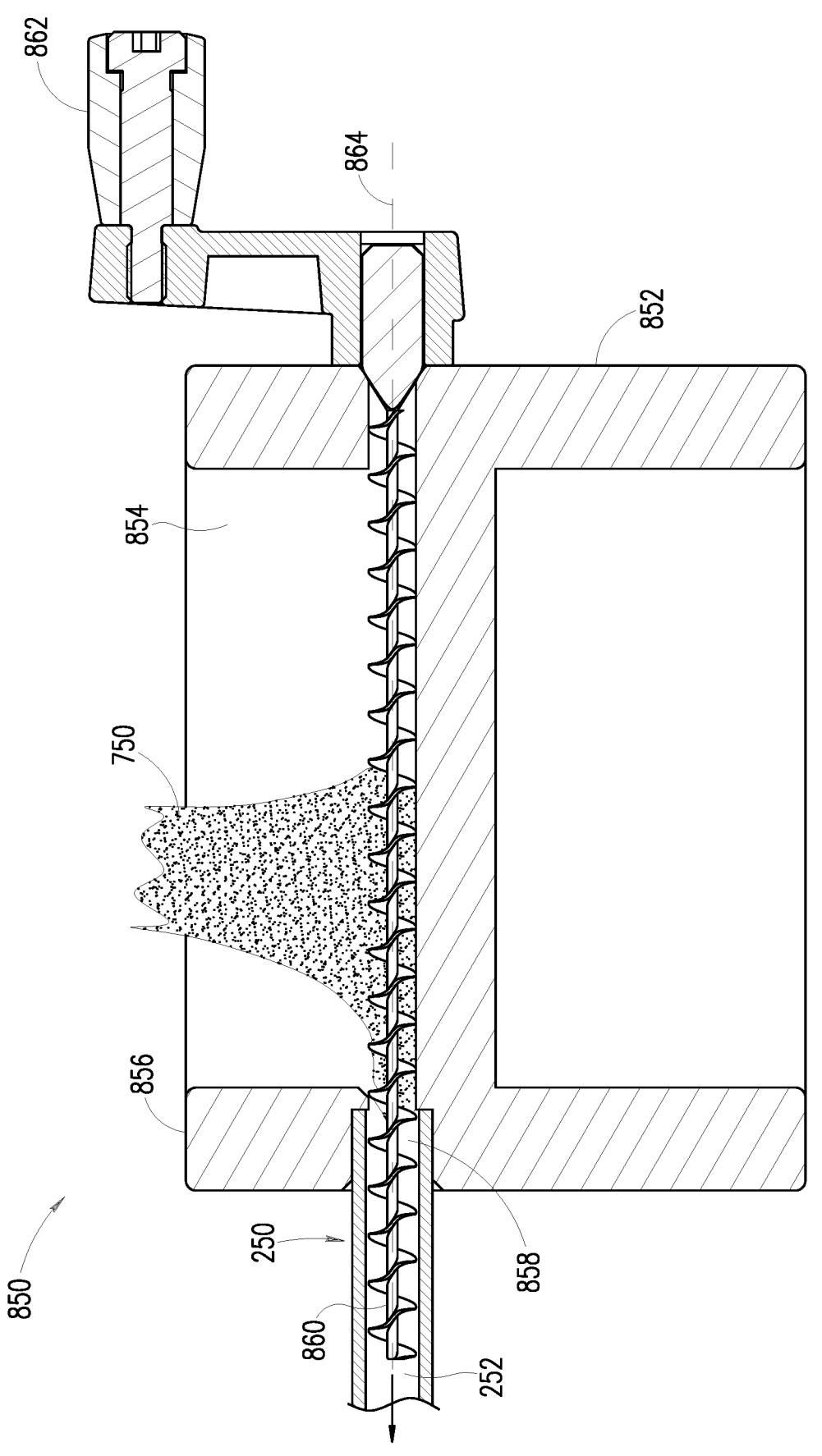
FIG. 31 is a cross-sectional view of the bone graft loader illustrated in FIG. 30.
Figure 32:
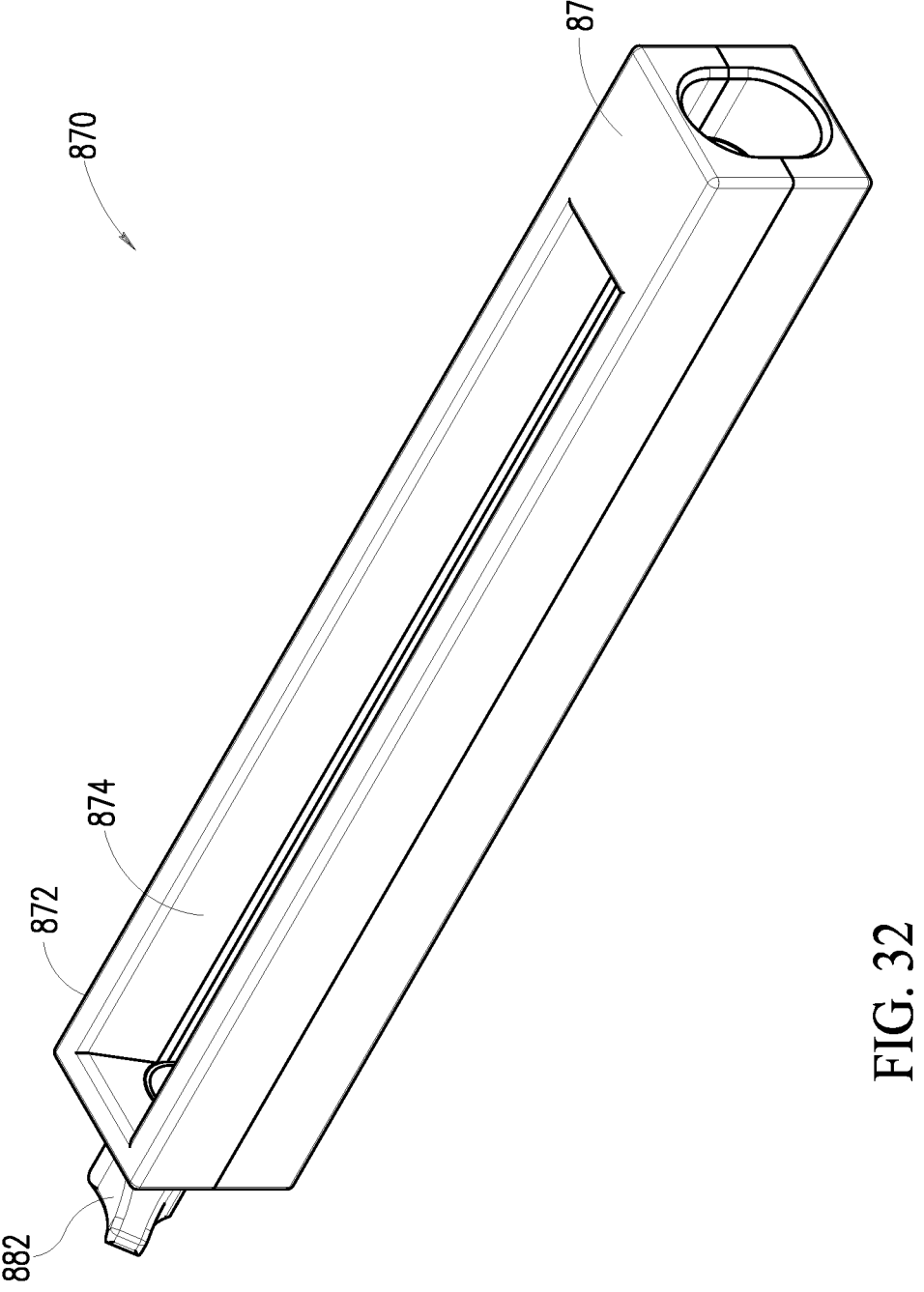
FIG. 32 is a front isometric view of a bone graft loader.
Figure 33:
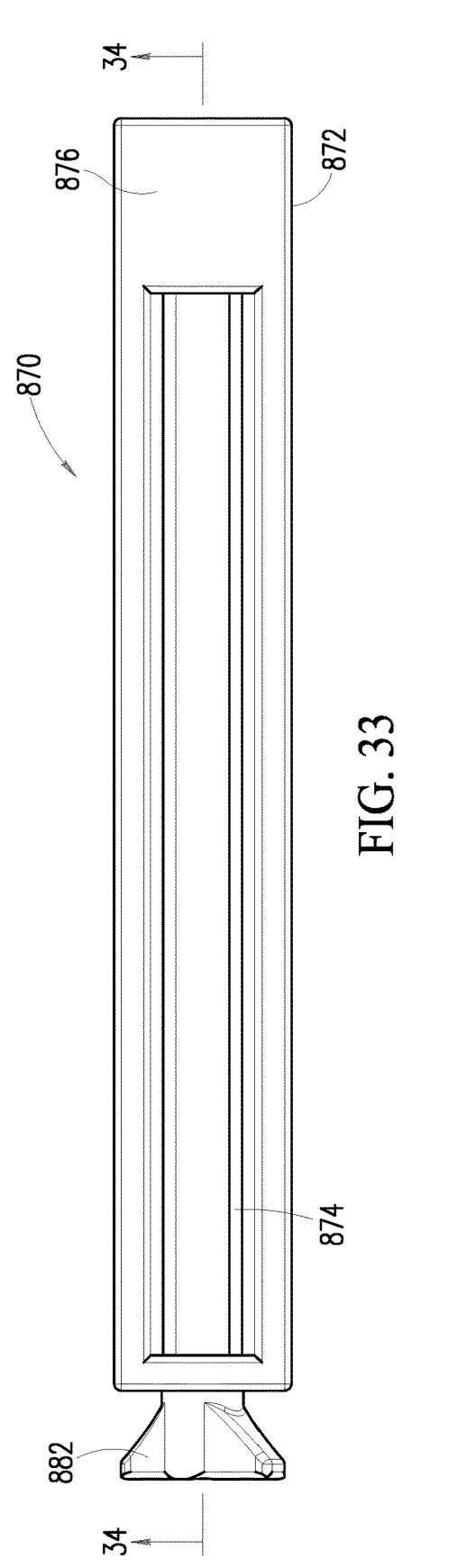
FIG. 33 is a top plan view of the bone graft loader illustrated in FIG. 32.

Referring to FIGS. 29 to 31, a bone graft loader 850 may include a frame 852 and define a funnel 854 that extends into the frame 852 (e.g., through a top surface 856, where the funnel 854 is wider, to a channel 858 (e.g., where the funnel 854 is thinner). The funnel 854 may be shaped so as to collect the bone graft material 750 dropped into the bone graft loader 850 (e.g., from above) and direct the bone graft material 750 toward the channel 858.

The bone graft loader 850 may further include an auger 860 positioned within the channel 858. As shown, the auger 860 may be coupled to a handle 862 such that rotation of the handle 862 rotates the auger 860 (e.g., within the channel 858 about an axis of rotation 864). Rotating the auger 860 may move the bone graft material 750 that is within the channel 858 (e.g., captured between flutes of the auger 860) along a direction that is parallel to the axis of rotation 864.

The cannula 250 may be positioned in proximity to (e.g., adjacent) the frame 852 such that the lumen 252 is aligned with the channel 858. The cannula 250 may be directly coupled to/abutting with the frame 852 (e.g., such that a portion of the auger 860 enters the lumen 252, as shown in FIG. 31). Alternatively, the bone graft loader 850 may include a connector or port (not shown) that fluidly connects the lumen 252 to the channel 858, allowing passage of the bone graft material 750 from the frame 852 bone graft loader 850 to the cannula 250.

The bone graft loader 850, and components thereof, may be used separately from or as a part of the bone graft delivery system 150 (e.g., instead of the bone graft loader 700). Accordingly, one embodiment of the bone graft delivery system 150 includes the bone graft loader 850, and an embodiment of the bone graft loader 850 may be made, sold, and/or used independently from a bone graft delivery system (e.g., the bone graft delivery system 150).

Referring to FIGS. 32 to 35, a bone graft loader 870 may include a frame 872 and define a funnel 874 that extends into the frame 872 (e.g., through a top surface 876, where the funnel 874 is wider, to a channel 878 (e.g., where the funnel 874 is thinner). The funnel 874 may be shaped so as to collect the bone graft material 750 dropped into the bone graft loader 870 (e.g., from above) and direct the bone graft material 750 toward the channel 878.

Figure 34:
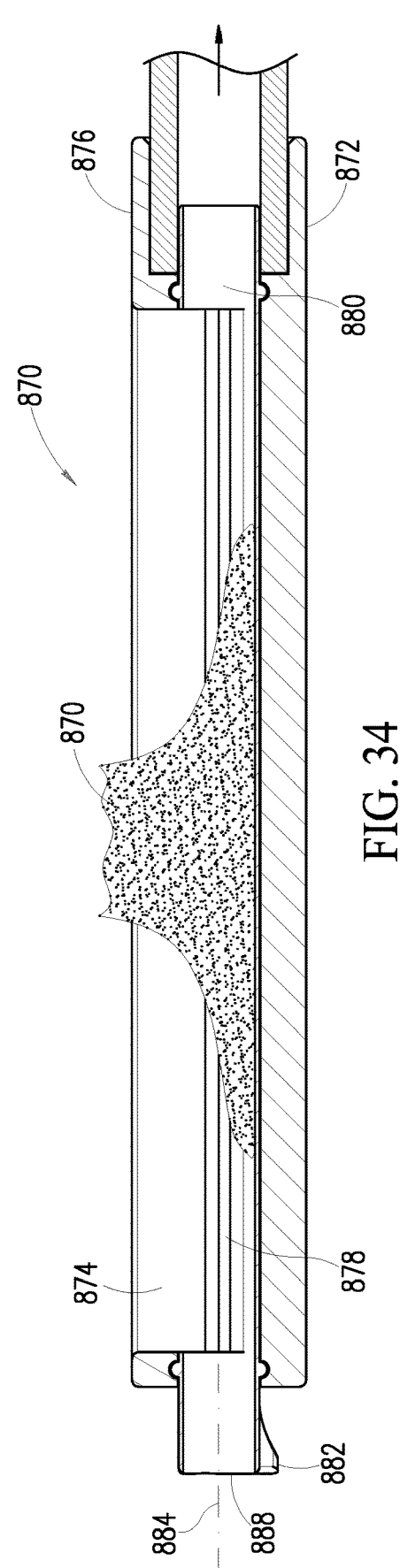
FIG. 34 is a cross-sectional view of the bone graft loader illustrated in FIG. 33 in a loading configuration.
Figure 35:
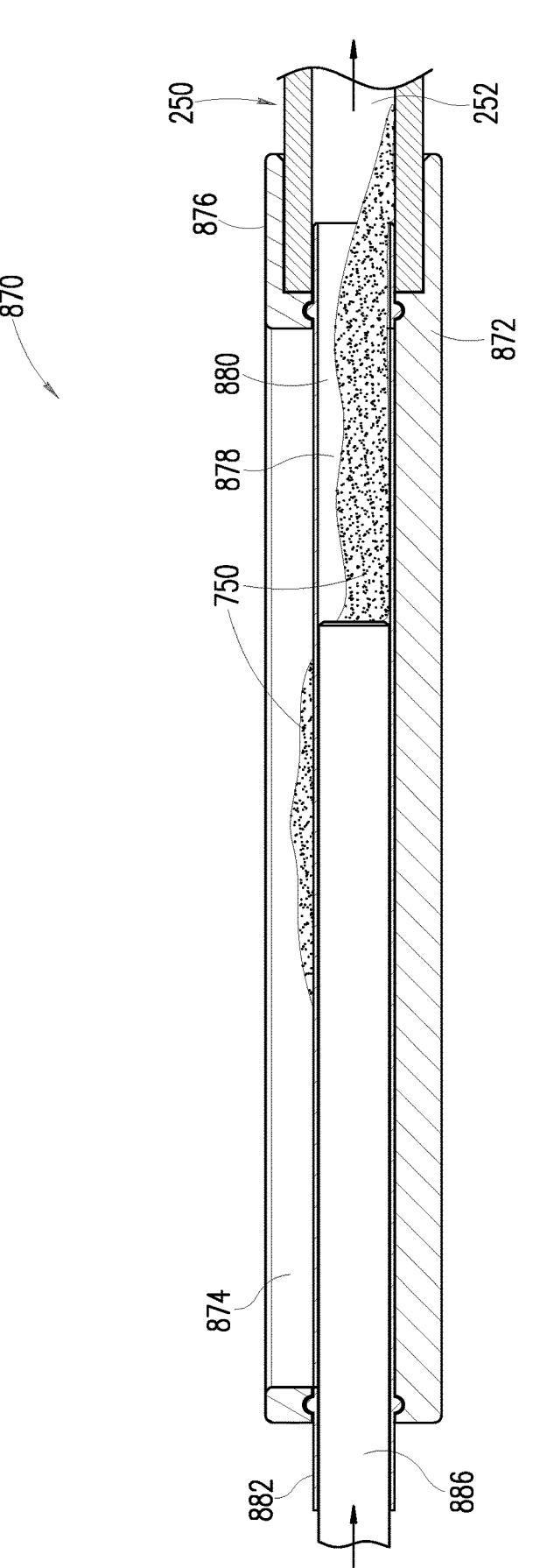
FIG. 35 is a cross-sectional view of the bone graft loader illustrated in FIG. 34 in a delivery configuration.

The bone graft loader 870 may further include a cartridge 880 positioned within the channel 878. As shown, the cartridge 880 may be coupled to a handle 882 such that rotation of the handle 882 rotates the cartridge 880 (e.g., within the channel 878 about an axis of rotation 884). The cartridge 880 may have a cross-sectional shape with an open perimeter (e.g., a trough shape), and rotating the cartridge 880 may close/block entrance into the channel 878. The bone graft loader 870 may have a loading configuration (as shown in FIG. 34) in which the open perimeter is aligned with the funnel 874, and a delivery configuration (as shown in FIG. 35) in which a closed portion of the perimeter is aligned with the funnel 874.

The cannula 250 may be positioned in proximity to (e.g., adjacent) the frame 872 such that the lumen 252 is aligned with the channel 878. The cannula 250 may be directly coupled to/abutting with the frame 872 (e.g., such that a portion of the cartridge 880 enters the lumen 252, as shown in FIG. 35). Alternatively, the bone graft loader 870 may include a connector or port (not shown) that fluidly connects the lumen 252 to the cartridge 880. A push rod or plunger 886 may be advanced into cartridge 880 (e.g., through an opening 888 that passes through the handle 882 and is aligned with the axis of rotation 884), thereby moving the bone graft material 750 through the cartridge 880 until the bone graft material 750 exits the bone graft loader 870 and enters the cannula 250.

The bone graft loader 870, and components thereof, may be used separately from or as a part of the bone graft delivery system 150. Accordingly, one embodiment of the bone graft delivery system 150 includes the bone graft loader 870, and an embodiment of the bone graft loader 870 may be made, sold, and/or used independently from a bone graft delivery system (e.g., the bone graft delivery system 150).

Referring to FIGS. 7 to 36 a kit 800 may include the delivery gun 450, the cannula 250, and the plunger 550. The kit 800 may further include one or more of the sleds 702 and one or more of the push rods 722. According to one embodiment, the kit 800 may include the deflector 630 couplable to the proximal end 452 of the delivery gun 450 so as to deflect a portion of the plunger 550 that extends proximally from the proximal end 452 away from the longitudinal axis 460.

Figure 36:
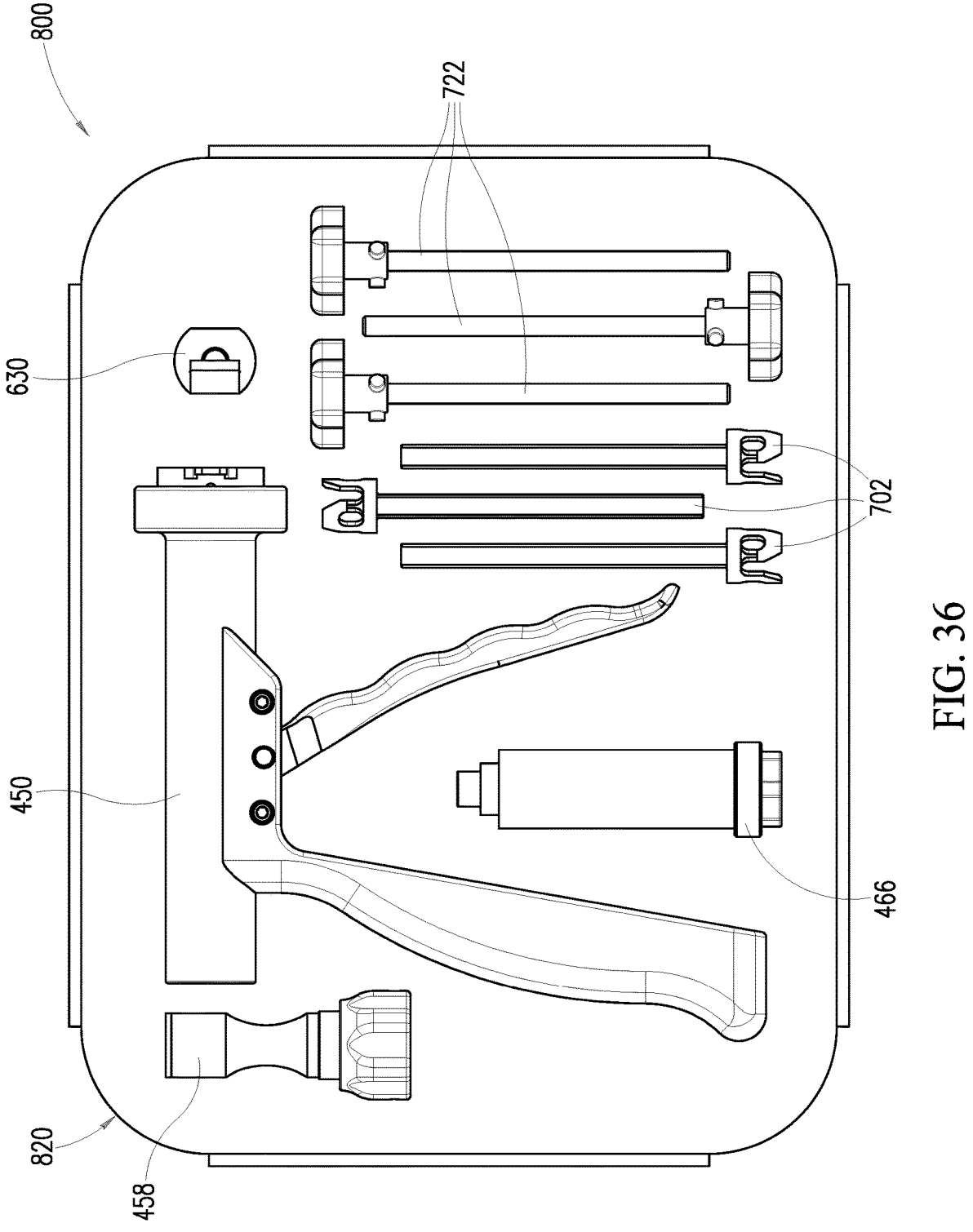
FIG. 36 is a top plan view of a kit that includes components of the bone graft delivery system illustrated in FIG. 7 and the bone graft loader illustrated in FIG. 28.

The kit 800 may further include the first circumferential engagement mechanism 466 (e.g., the first tubular member 622 enclosing the first split ring 602 and the first spring 610), and the second circumferential engagement mechanism 468 (e.g., the second tubular member 624 enclosing the second split ring 612 and the second spring 620). As shown in FIG. 36, the kit 800 may include a sterilization case 820 that separately (e.g., in the disassembled configuration) receives each of the delivery gun 450, the deflector 630, the first circumferential engagement mechanism 466 (e.g., the first tubular member 622 enclosing first split ring 602 and the first spring 610), and the second circumferential engagement mechanism 468 (e.g., the second tubular member 624 enclosing second split ring 612 and the second spring 620) in an interior of the sterilization case 820. The sterilization case 820 may be closed (e.g., enclosing the components of the kit 800 therein) and supplied with steam to sterilize the enclosed components of the kit 800).

Bone graft material can include crushed bone (cancellous and cortical), or a combination of these (and/or other natural materials) and can further comprise synthetic biocompatible materials. Bone graft material can be provided in a gel or slurry form or a dry or granule form that can be rehydrated before use. Bone graft materials occur in varying degrees of liquidity and viscosity.

Any suitable bone graft material can be delivered using the devices described herein. Bone graft material can stimulate growth of healthy bone. Bone graft material can be mixed with any liquid or therapeutic agent, powder, fiber, or granular material prior to loading into the offset cannula.

Bone graft material includes natural and/or inorganic material such as, for example, inorganic ceramic and/or bone substitute material. The bone material can also include natural bone material such as, for example, bone which is cortical, cancellous, or cortico-cancellous of autogenous, allogenic, xenogenic, or transgenic origin. In some embodiments, bone material can include demineralized bone material such as, for example, substantially demineralized bone material, partially demineralized bone material, or fully demineralized bone material.

Bone graft material can comprise crushed bone (cancellous and cortical), other natural materials, synthetic biocompatible materials, or combinations thereof. Bone graft materials can be made up entirely of natural materials, entirely of synthetic biocompatible materials, or any combination of these materials. Bone graft material can be in a gel, paste, slurry, or other suitable form.

Bone graft material can include growth factors such as naturally occurring or genetically engineered growth factors, which can promote bone formation. Naturally occurring or genetically engineered growth factors that can be used in bone graft material include, for example, members of the fibroblast growth factor family, including acidic and basic fibroblast growth factor (FGF-1 and FGF-2) and FGF-4; members of the platelet-derived growth factor (PDGF) family, including PDGF-AB, PDGF-BB and PDGF-AA; EGFs; VEGF; members of the insulin-like growth factor (IGF) family, including IGF-I and -II; the TGF-β superfamily, including TGF-β1, 2 and 3; osteoid-inducing factor (OIF), angiogenin(s); endothelins; hepatocyte growth factor and keratinocyte growth factor; members of the bone morphogenetic proteins (BMPs) BMP-1, BMP-3, BMP-2, OP-1, BMP-2A, BMP-2B, BMP-7 and MP-14, including HBGF-1 and HBGF-2; growth differentiation factors (GDFs), members of the hedgehog family of proteins, including indian, sonic and desert hedgehog; ADMP-1; bone-forming members of the interleukin (IL) family; rhGDF-5; and members of the colony-stimulating factor (CSF) family, including CSF-1, G-CSF, and GM-CSF; and isoforms thereof.

A bone graft material can be a porous matrix that can contain porous or semi-porous collagen, extracellular matrices, metals (such as titanium, cobalt-chromium (CoCr), and stainless steel), polymers (such as polyether ether ketone (PEEK), polyethylene, polypropylene, and polyethylene terephthalate (PET)) resorbable polymers (such as polylactic acid (PLA), polydiacetylenes (PDAs), poly(ethylene oxide) (PEO), polyethylene glycol (PEG), poly(vinyl alcohol) (PVA), and capralactides), bone substitutes (such as B-tricalcium phosphate (B-TCP), osteoconductive hydroxyapatite (HA), poorly crystalline apatitic calcium phosphate (PCA) and calcium phosphate (CaP)-based biomaterials), autograft, allograft, xenograft, and/or blends thereof.

In some embodiments, a porous matrix bone graft material is a mineral. A mineral can be, e.g., calcium, phosphorus, or combinations thereof. In some aspects, a mineral is calcium phosphate, tricalcium phosphate, hydroxyapatite, or combinations thereof. A bone graft material matrix can comprise a hydrogel or can incorporate a hydrogel as component, which can expand and enhance filling and/or improve handling characteristics.

Referring to FIGS. 1 to 6, bone graft delivery systems can be used by loading the detachable offset cannula with bone graft material using a delivery sled. One or more delivery sleds can be loaded with, for example, a bone graft material. The sled can be loaded from the open top or open side by pouring or pushing the bone graft material into the sled. A rod, plunger, spatula or other suitable tool can be used to load the bone graft material into the one or more delivery sleds. The delivery sleds can be attached via a connector or brought into proximity of an inlet 209 of an offset cannula and the bone graft material can be poured or pushed into the offset cannula. Once filled with the desired amount of bone graft material, the offset cannula can be attached via a connector to a distal end 403 of the delivery gun 400.

A flexible plunger can be inserted into the lumen 411 of the delivery gun. The tip of the detachable offset cannula of the bone graft delivery system can be guided to the desired site (e.g., a surgical site such as the spine). The trigger of the delivery gun can be depressed by a user such that a first circumferential engagement mechanism is pushed down onto the flexible plunger and forward. This causes the flexible plunger to move forward down the cannula of the delivery gun. A second circumferential engagement mechanism can prevent the plunger from moving backwards towards the proximal end 402 of the delivery gun in some aspects. The plunger can move into the offset cannula and therefore push the bone graft material out of the tip of the cannula and into the desired use site. The plunger can move all the way to the tip of the cannula or can move only partially into the cannula.

After the desired amount of bone graft material has been dispensed, the disengagement mechanism can be activated to release the flexible plunger. The offset cannula can be removed from the delivery gun by releasing the connector. According to one embodiment, the flexible plunger does not need to be removed from the delivery gun to remove the offset cannula.

Provided herein are methods of delivering bone graft material to a surgical site, e.g., an intervertebral site. The methods comprise guiding the tip, e.g., the oval shaped tip, of the detachable offset cannula of the bone graft delivery system to the surgical site, activating the trigger of the delivery gun, and delivering bone graft material to the surgical site.

Devices described herein can be used in, for example, minimally invasive spine procedures such as posterior lumbar fusion (PLF), posterior lumbar interbody fusion (PLIF), anterior lumbar interbody fusion (ALIF), circumferential 360 fusion, transforaminal lumbar interbody fusion (TLIF), and direct lateral interbody fusion (D-LIF).

A surgeon can harvest bone or other biological factors from a patient and process the bone using any suitable method to make a bone graft material. Alternatively, a bone graft material can be prepared from synthetic and/or allogenic materials. Once prepared one or more delivery sleds can be filled with the bone graft material. The one or more delivery sleds can be brought into proximity with or connected to an offset cannula. The bone graft material can be delivered to the cannula by pouring, pushing with a plunger or rod, or any other suitable method. Multiple delivery sleds can be used to load the offset cannula or one sled can be refilled to add additional bone graft material to the offset cannula until the cannula is filled or all of the bone graft material is utilized. The delivery sled or sleds are removed from the offset cannula.

The loaded offset cannula can be introduced to the surgical site and then loaded onto the connector of the delivery gun. Alternatively, the loaded offset cannula can be connected to the connector of the distal end 403 of the delivery gun and then the offset cannula can be brought to the surgical site.

Provided herein are kits comprising one or more of a delivery gun, offset cannula, flexible plunger, one or more (e.g., 1, 2, 3, 4, 5, 6, 10, 15 or more) delivery sleds, delivery tools (e.g., rods, plungers, spatulas) for transferring bone graft material to delivery sleds and from the delivery sleds into the offset cannula, and one or more types of bone graft materials, bone material, or growth factors.

The terms used in the specification generally have their ordinary meanings in the art, within the context of the compositions and methods described herein, and in the specific context where each term is used. Some terms have been more specifically defined herein to provide additional guidance to the practitioner regarding the description of the compositions and methods.

As used herein, the term "and/or" includes any and all combinations of one or more of the associated listed items. As used in the description herein and throughout the claims that follow, the meaning of "a", "an", and "the" includes plural reference as well as the singular reference unless the context clearly dictates otherwise. The term "about" in association with a numerical value means that the value varies up or down by 5%. For example, for a value of about 100, means 95 to 105 (or any value between 95 and 105).

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising," "consisting essentially of," and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present methods and compositions have been specifically disclosed by embodiments and optional features, modifications and variations of the concepts herein disclosed can be resorted to by those skilled in the art, and that such modifications and variations are considered to be within the scope of the compositions and methods as defined by the description and the appended claims.

Any single term, single element, single phrase, group of terms, group of phrases, or group of elements described herein can each be specifically excluded from the claims.

Whenever a range is given in the specification, for example, a temperature range, a time range, a composition, or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods.

In addition, where features or aspects of the compositions and methods are described in terms of Markush groups or other grouping of alternatives, those skilled in the art will recognize that the compositions and methods are also thereby described in terms of any individual member or subgroup of members of the Markush group or other group.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The various embodiments described above can be combined to provide further embodiments.

The methods described herein can be performed with variations. For example, many of the methods may include additional acts, omit some acts, and/or perform acts in a different order than as illustrated or described.

These and other changes can be made to the embodiments in light of the above-detailed description. In general, in the following claims, the terms used should not be construed to limit the claims to the specific embodiments disclosed in the specification and the claims but should be construed to include all possible embodiments along with the full scope of equivalents to which such claims are entitled. Accordingly, the claims are not limited by the disclosure.

The invention claimed is:

1. A bone graft delivery system comprising:
   a delivery gun comprising a proximal end, a distal end, and a body extending therebetween, the body defining a first lumen extending through the body from the proximal end to the distal end along a longitudinal axis;

a cannula coupled to the distal end of the delivery gun, the cannula defining a second lumen extending through the cannula along a first portion that is aligned with the longitudinal axis, and a second portion that is angularly offset from the longitudinal axis; and a flexible plunger sized to be insertable into the first lumen through an opening defined by the proximal end, and the flexible plunger is movable to a position wherein a distal portion of the flexible plunger is within the second portion of the second lumen and a proximal portion of the flexible plunger is within the first lumen, wherein the cannula includes a connector and the delivery gun includes a hub with corresponding features that engage to couple the cannula to the delivery gun, and wherein the corresponding features include at least one track and at least one follower sized to fit within and ride along the track, one of the connector and the hub includes the at least one track, and the other of the connector and the hub includes the at least one follower, a first portion of the at least one track extending into the one of the connector and the hub along a first direction, and a second portion of the at least one track extending into the one of the connector and the hub within a plane that is normal to the first direction.

2. The bone graft delivery system of claim 1, wherein cannula is detachable from the delivery gun when a portion of the flexible plunger is within the second lumen.

3. The bone graft delivery system of claim 1 wherein the second portion extends along a cannula axis, and the cannula axis is angularly offset from the longitudinal axis by an angle that is between 90 and 170 degrees.

4. The bone graft delivery system of claim 3 wherein the angle is adjustable.

5. The bone graft delivery system of claim 1 wherein the cannula has a proximal end that is coupled to the distal end of the delivery gun and terminates at a distal end, wherein the distal end has an oval shaped outer perimeter.

6. The bone graft delivery system of claim 5 wherein a cross-sectional area of the second lumen remains constant from the proximal end of the cannula to the distal end of the cannula.

7. The bone graft delivery system of claim 1 wherein the corresponding features are engageable to couple the cannula to the delivery gun in a plurality of orientations.

8. The bone graft delivery system of claim 1 wherein the corresponding features further include a spring biased member and a recess sized to receive at least a portion of the spring biased member, one of the connector and the hub includes the spring biased member, and the other of the connector and the hub includes the recess, and wherein the recess is aligned with and receives at least a portion of the spring biased member when the follower reaches an end of the at least one track after following both the first portion of the at least one track and the second portion of the at least one track.

9. The bone graft delivery system of claim 1, further comprising:

a sled having an elongate body, the elongate body defining a channel extending through the sled; and a push rod having an elongate body with a rod portion shaped to correspond to the channel such that the rod portion is slidable within the channel.

10. The bone graft delivery system of claim 9 wherein the elongate body of the sled includes a trough with an open cross-sectional shape such that the channel is accessible along a length of the trough.

11. A bone graft delivery system comprising:

a delivery gun comprising a proximal end, a distal end, and a body extending therebetween, the body defining a first lumen extending through the body from the proximal end to the distal end along a longitudinal axis;

a cannula coupled to the distal end of the delivery gun, the cannula defining a second lumen extending through the cannula along a first portion that is aligned with the longitudinal axis, and a second portion that is angularly offset from the longitudinal axis; and a flexible plunger sized to be insertable into the first lumen through an opening defined by the proximal end, and the flexible plunger is movable to a position wherein a distal portion of the flexible plunger is within the second portion of the second lumen and a proximal portion of the flexible plunger is within the first lumen, wherein the delivery gun includes a trigger, a first circumferential engagement mechanism, and a second circumferential engagement mechanism, and wherein when the trigger is engaged the first circumferential engagement mechanism advances the flexible plunger within the first lumen toward the distal end, and when the trigger is disengaged the second circumferential engagement mechanism prevents movement of the flexible plunger toward the proximal end.

12. The bone graft delivery system of claim 11, further comprising:

an assembled configuration wherein the first circumferential engagement mechanism and the second circumferential engagement mechanism are positioned within the first lumen; and a disassembled configuration wherein the first circumferential engagement mechanism and the second circumferential engagement mechanism are removed from the first lumen, wherein the bone graft delivery system is transitional between the assembled configuration and the disassembled configuration without plastic deformation.

13. The bone graft delivery system of claim 12 wherein the first circumferential engagement mechanism comprises:

a first split ring with a first inner surface that includes a plurality of teeth that correspond to the flexible plunger, and a first tapered outer surface; and a first spring exerting a first biasing force toward the first split ring and toward the proximal end, and wherein the second circumferential engagement mechanism comprises:

a second split ring with a second inner surface that includes a plurality of teeth that correspond to the flexible plunger, and a second tapered outer surface;

a second spring exerting a second biasing force toward the second split ring and toward the proximal end.

14. The bone graft delivery system of claim 13, further comprising:

a first tubular member that encloses the first split ring and the first spring; and a second tubular member that encloses the second split ring and the second spring, wherein the first tubular member with the first split ring and the first spring enclosed therein is removable from the first lumen, and the second tubular member with the second split ring and the second spring enclosed therein is removable from the first lumen to transition the bone graft delivery system from the assembled configuration to the disassembled configuration.

15. A bone graft delivery system comprising:

a delivery gun comprising a proximal end, a distal end, and a body extending therebetween, the body defining a first lumen extending through the body from the proximal end to the distal end along a longitudinal axis;

a cannula coupled to the distal end of the delivery gun, the cannula defining a second lumen extending through the cannula along a first portion that is aligned with the longitudinal axis, and a second portion that is angularly offset from the longitudinal axis; and a flexible plunger sized to be insertable into the first lumen through an opening defined by the proximal end, and the flexible plunger is movable to a position wherein a distal portion of the flexible plunger is within the second portion of the second lumen and a proximal portion of the flexible plunger is within the first lumen, a deflector coupled to the proximal end of the delivery gun, the deflector positioned so as to deflect a portion of the flexible plunger that extends proximally from the proximal end away from the longitudinal axis.

16. A bone graft delivery system comprising:

a delivery gun comprising a proximal end, a distal end, and a body extending therebetween, the body defining a first lumen extending through the body from the proximal end to the distal end along a longitudinal axis;

a cannula coupled to the distal end of the delivery gun, the cannula defining a second lumen extending through the cannula along a first portion that is aligned with the longitudinal axis, and a second portion that is angularly offset from the longitudinal axis; and a flexible plunger sized to be insertable into the first lumen through an opening defined by the proximal end, and the flexible plunger is movable to a position wherein a distal portion of the flexible plunger is within the second portion of the second lumen and a proximal portion of the flexible plunger is within the first lumen;

a sled having an elongate body, the elongate body defining a channel extending through the sled, wherein the elongate body of the sled includes a collar extending away from the channel, the elongate body of the sled defining a collar track that extends into the collar toward the channel along a non-linear path; and a push rod having an elongate body with a rod portion shaped to correspond to the channel such that the rod portion is slidable within the channel, wherein the elongate body of the push rod includes a handle extending from the rod portion, the handle including a projection shaped to follow the non-linear path of the collar track.

17. A bone graft loader comprising:

a sled having an elongate body, the elongate body including a tubular member defining a channel extending therethrough, the elongate body further including a collar extending from the tubular member, the collar defining a collar track extending into the collar toward the tubular member, the collar track including a non-linear portion; and a push rod having an elongate body with a rod portion shaped to correspond to the channel such that the rod portion is slidable within the channel, the elongate body of the push rod further including a handle extending from the rod portion, and a projection shaped to follow the non-linear portion of the collar track.

* * * * *